United States Patent [19]

Umezawa et al.

[11] 4,297,485

[45] Oct. 27, 1981

[54] PRODUCTION OF A SELECTIVELY PROTECTED N-ACYLATED DERIVATIVE OF AN AMINOGLYCOSIDIC ANTIBIOTIC

[75] Inventors: Hamao Umezawa; Sumio Umezawa, both of Tokyo; Tsutomu Tsuchiya; Yasushi Takagi, both of Yokohama; Tomo Jikihara, Kawasaki, all of Japan

[73] Assignee: Zaidan Hojin Biseibutsu Kagaku Kenkyu Kai, Tokyo, Japan

[21] Appl. No.: 90,591

[22] Filed: Nov. 2, 1979

[30] Foreign Application Priority Data

Nov. 11, 1978 [JP] Japan .................... 53-138402
Jun. 12, 1979 [JP] Japan .................... 54-73064

[51] Int. Cl.$^3$ .................................... C07H 15/22
[52] U.S. Cl. .................................... 536/10; 536/12; 536/17 R
[58] Field of Search .................. 536/10, 17 R, 12

[56] References Cited

U.S. PATENT DOCUMENTS

| | | | |
|---|---|---|---|
| 3,781,268 | 12/1973 | Kawaguchi et al. | 536/10 |
| 3,919,190 | 11/1975 | Barker et al. | 536/10 |
| 3,925,354 | 12/1975 | Umezawa et al. | 536/17 R |
| 3,939,143 | 2/1976 | Umezawa et al. | 536/10 |
| 3,940,382 | 2/1976 | Umezawa et al. | 536/10 |
| 4,001,208 | 1/1977 | Umezawa et al. | 536/10 |
| 4,055,715 | 10/1977 | Tomioka et al. | 536/17 R |
| 4,107,424 | 8/1978 | Umezawa et al. | 536/10 |
| 4,136,254 | 1/1979 | Nagabhushan et al. | 536/10 |

*Primary Examiner*—Johnnie R. Brown
*Attorney, Agent, or Firm*—Larson and Taylor

[57] ABSTRACT

Aminoglycosidic antibiotic comprising a 6-0-(3″-aminoglycosyl)-2-deoxystreptamine optionally having a 4-0-(aminogycosyl) group, such as kanamycins, gentamicins, sisomicin, forms reversible complex with zinc cations by association of the zinc cations with some pairs of aminohydroxyl groups in the aminoglycoside, and the zinc-complexed amino groups are blocked from acylation. Reaction of this zinc complex with an acylation reagent having an amino-blocking acyl group brings about acylation of the non-complexed amino groups to give an N-acylated zinc complex, namely a complex of zinc cation with an N-acylated aminoglycosidic antibiotic derivative. Removal of zinc cations from N-acylated zinc complex yields a partially N-acylated aminoglycosidic antibiotic where 1- and 3″-amino groups are unprotected but all other amino groups protected with acyl group. Further reaction of this partially N-acylated product with a certain alkanoic acid or N-formyl-imidazole results in preferential acylation of 3″-amino group without 1-amino group being acylated, affording a 1-N-unprotected and other N-fully-protected derivative of the aminoglycosidic antibiotic which is valuable to be 1-N-acylated with α-hydroxy-ω-aminoalkanoic acid for high-yield production of known semi-synthetic 1-N-(α-hydroxy-ω-aminoalkanoyl)-aminoglycosidic antibiotic.

20 Claims, No Drawings

PRODUCTION OF A SELECTIVELY PROTECTED N-ACYLATED DERIVATIVE OF AN AMINOGLYCOSIDIC ANTIBIOTIC

FIELD OF INVENTION

This invention relates to some new processes for the production of a selectively protected N-acylated derivative of an aminoglycosidic antibiotic in which some amino or alkylamino groups at particular positions of the aminoglycoside molecule have selectively been protected or blocked with an acyl group. This invention thus relates to new processes for selectively protecting some amino or alkylamino groups at particular positions of the aminoglycosidic antibiotic. This invention finds its main uses in the production of a selectively protected N-acylated derivative of the aminoglycosidic antibiotic which comprises a deoxystreptamine moiety having a 3"-aminoglycosyl group linked with 6-hydroxyl group of the deoxystreptamine moiety in the aminoglycoside molecule. The aminoglycosidic antibiotic to which this invention is applicable may be defined more specifically as an aminoglycosidic antibiotic consisting of a 6-O-(3"-amino or 3"-alkylamino-3"-deoxyglycosyl)-2-deoxystreptamine which may optionally have a 4-O-(6'-aminoglycosyl) substituent, and typical examples are kanamycins, gentamicins, sisomicin, netilmicin and verdamicin. This invention further includes an application of these new processes to the production of a 1-N-(α-hydroxy-ω-aminoalkanoyl)-amino-glycosidic antibiotics which are known as useful semi-synthetic antibacterial agent active against drug-resistant bacteria.

PRIOR ART

Aminoglycosidic antibiotics such as kanamycins are the substance containing several amino functions and hydroxyl functions having relatively high and various degrees of reactivity. Many kinds of semi-synthetic aminoglycosidic antibiotics derived from the parent aminoglycosidic antibiotics have been synthesized. In the semi-synthesis of these derivatives, it is often necessary or preferable to ensure that some amino groups and/or some hydroxyl groups in the staring aminoglycosidic antibiotic have selectively been protected or blocked with one or more suitable protective groups.

For selective protection of amino groups and/or hydroxyl groups in the aminoglycosidic antibiotic, various, successful methods have been developed and are available as far as selective protection of hydroxyl group is concerned with. However, for selective protection of particular some amino groups amongst the existing many amino groups of the aminoglycosidic antibiotic, the presently available methods for this purpose are either difficult to operate or require some complicated operations. This is because all the amino groups in the aminoglycosidic antibiotic have no great difference in their reactivity. As a demonstrative example is provided by 6'-amino group of kanamycin A, however, such an amino or methylamino group which is bound with a certain carbon atom which is, in turn, linking to only one carbon atom in the aminoglycoside molecule exhibits a higher reactivity than that of the amino or methylamino group which is bounded with a certain carbon atom which is linking to two or more carbon atoms in this aminoglycoside molecule. For this reason the former type of amino or methylamino group is able to much more preferentially react with an acylation reagent having an acyl group to be introduced as the amino-protecting group, as compared to the latter type of amino or methylamino group, whereby the N-protected derivative having the former type of amino or methylamino group preferentially blocked with the acyl group may be produced in a higher yield than the otherwise N-protected derivatives. Several years ago, some of the present inventors found that when amino group and hydroxyl group are neighboring to each other in a pair in the steric configuration of the molecule of the aminoglycosidic antibiotic, these amino and hydroxyl groups can selectively be combined with each other into the form of a cyclic carbamate by treatment with sodium hydride, so that the pair of amino and hydroxyl groups can be blocked simultaneously in the cyclic carbamate without blocking the other amino groups present in the same molecule (see "Journal of Antibiotics", 25, No. 12, 741–742 (1972); U.S. Pat. No. 3,925,354 and 3,965,089).

In a recent year, Nagabhushan et al have found that when a salt of a divalent transition metal ($M^{++}$) selected from the group consisting of copper (II), nickel (II), cobalt (II) and cadmium (II) is reacted in an inert organic solvent with an aminoglycosidic antibiotic which belongs to the class of 4-O-(aminoglycosyl)-6-O-(aminoglycosyl)-2-deoxystreptamines represented by kanamycins, gentamicins and sisomicin, this divalent transition metal cation is complexed with a pair of amino and hydroxyl groups which exist at the particular positions of "vicinal" relationship in the aminoglycoside molecule, whereby the aminoglycosidic antibiotic-transition metal cation complex is formed (see Japanese Patent Application Pre-publication Sho-52-153944 and U.S. patent application Ser. No. 697,297 now granted under U.S. Pat. No. 4,136,254 issued on Jan. 23, 1979). In this aminoglycosidic antibiotic-transition metal cation complex, the complexed amino group is being blocked with the divalent transition metal cation. When this complex is subsequently reacted with an acylation reagent having an acyl group, only the non-complexed amino groups in the metal complex which are not blocked by the divalent metal cation can be acylated mainly, so that selective N-protection with the acyl group is achieved. This is illustrated below with reference to kanamycin A as an example. Thus, when a divalent transition metal cation ($M^{++}$) chosen from cupper (II), nickel (II), cobalt (II) and cadmium (II) cations is reactd with kanamycin A, complexing reaction of the divalent metal cation ($M^{++}$) occurrs between 1-amino group and 2"-hydroxy group and between 3"-amino group and 4"-hydroxyl group of kanamycin A molecule, shown by the formula (I) below.

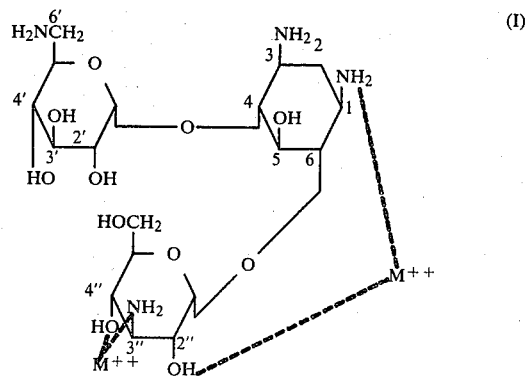

In the above complexing reaction, therefore, it is seen that at least 2 mol of the transition metal salt is required for 1 mol of kanamycin A. In the resultant metal complex, 1-amino and 3''-amino groups are blocked at the same time. When this complex of the formula (I) is treated with an acylation reagent having an acyl group which is available as an amino-protecting group known in the conventional synthesis of polypeptides, the non-complexed 3-amino and 6'-amino groups only are acylated mainly to give 3,6'-di-N-acylated derivative (see "Journal of American Chemical Society" 100, 5253–5254 (1978)).

We have recognized the above fact as reported, but we still have made our further researches on the interaction of another, various metal cations with aminoglycosidic antibiotics such as kanamycin A and kanamycin B as well as semisynthetic derivatives of the aminoglycosidic antibiotics. As a result, we have now found that although divalent zinc cation has behaviours significantly different from those of the above-mentioned divalent, nickel, cobalt, copper and cadmium cations, the zinc cation is ultimately able to strongly complex with and block both 1-amino (or 1-alkylamino) group and 3''-amino (or 3''-alkylamino) group of an aminoglycoside compound (such as kanamycin A, B or C) which comprises a deoxystreptamine moiety having a 3''-aminoglycosyl or 3''-alkylaminoglycosyl group linked to the 6-hydroxyl group of said deoxystreptamine moiety.

According to Nagabhushan et al, it might be expected that when divalent nickel, cobalt, copper or cadmium cation would be reacted with kanamycin B, for example, there should be formed a kanamycin B-metal salt complex of the following formula (II):

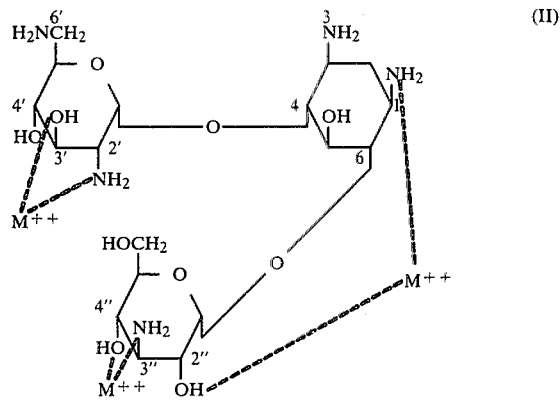

This expectation is supportable by the Nagabhushan et al's disclosure of the aforesaid "Journal of American Chemical Society" according to which vicinal amino-hydroxyl group pairs should form reversible complexes with the divalent transition metal cations, in view of the fact that kanamycin B contains three pairs of vicinal amino-hydroxyl groups between 1- and 2''-positions, between 2'- and 3'-positions and between 2''- and 3''-positions of the kanamycin B molecule. However, it has now been found that when kanamycin B is reacted with a divalent metal cation, zinc cation, the kanamycin B-zinc salt complex actually formed contains free 2'-amino and 3'-hydroxyl groups which are not being blocked by the zinc cation, as be contrary to the Nagabhushan's proposal. Even if complexing reaction of zinc cation with the 2'-amino and 3'-hydroxyl group occurs, the force of complexing is very low, so that substantially 2'-amino and 3'-hydroxyl groups are not being blocked in practice. Therefore, when the kanamycin B-zinc cation complex is then acylated by reacting eg. with N-benzyloxycarbonyloxysuccinimido to introduce benzyloxycarbonyl group as the amino-protecting acyl group, tri-3,2',6'-N-acylated derivative in which three, 3-, 2'- and 6'-amino groups have been acylated is produced, in fact, in a higher yield than the otherwise N-acylated derivatives, but then the 3,6'-di-N-acylated derivative actually cannot be obtained (refer to Example 19 given hereinafter). This experimental fact suggests that zinc cation shows a behaviour different from those of the aforesaid four transition metal cations particularly in that zinc cation does not complex with the vicinal 2'-amino and 3'-hydroxyl group pair.

As a further example, when kanamycin A is reacted with zinc cation followed by acylation with benzyloxycarbonyl group (refer to the formula (I) hereinbefore), the fact is observed that 3,6'-di-N-benzyloxycarbonylkanamycin A is formed as the main acylation product in case zinc cation is provided just in an amount of slightly more than 1 mol. per mol. of kanamycin A. In this case, it must be noticed that this acylation reaction gives formation of 1,3,6',3''-tetra-N-benzyloxycarbonyl derivative of kanamycin A and formation of non-acylated, initial kanamycin A simultaneously to some extent but actually brings about formation of tri-N-benzyloxycarbonyl derivative of kanamycin A only in a low yield, in spite of that the Nagabhushan et al's elucidation of the reaction mechanism might expect that the tri-N-benzyloxycarbonyl derivative would be formed in a higher yield than the other N-acylated derivatives (refer to Example 7 given hereinafter). In the specification and particularly claim 4 of U.S. Pat. No. 4,136,254, Nagabhushan et al have stated to the effect that a salt of a divalent transition metal such as copper (II), nickel (II), cobalt (II) etc., is necessary to be employed in a total quantity of at least 2 mol. per mol. of kanamycin A for the formation of kanamycin A-transition metal salt complex, as will be seen from the formula (I) given hereinbefore. Our experiment has revealed that, in contrast to the four transition metal cations, zinc cation is able to achieve the effect of blocking 1-amino and 3''-amino group of kanamycin A when zinc cation is employed in a total quantity of at least 1 mol per mol of kanamycin A. According to our test, it has been found that when a nickel salt is reacted in a quantity of slightly more than 1 mol for 1 mol of kanamycin A followed by acylation of the resulting kanamycin A-nickel salt complex with benzyloxycarbonyl group, there is obtained only in a very much low yield 3,6'-di-N-benzyloxycarbonylkanamycin A which would be obtainable in a significant yield when kanamycin A-zinc salt complex was acylated (see Example 7 hereinafter). In view of the above-mentioned facts, it is concluded that zinc (II) cation exhibits a mechanism of complexing with an aminoglycoside which is different from the complexing mechanism of nickel (II), cobalt (II), copper (II) and cadmium (II), cation, and that the aminoglycosidezinc cation complex has a complexing stability which is different from that of the complex of the aminoglycoside with nickel (II), cobalt (II), copper (II) or cadmium (II) cation. For the complexing of zinc cation with the aminoglycosidic antibiotic, zinc cation may be provided in the form of a zinc salt which is advantageously inexpensive and unlikely to be a source of polluting the environment.

DETAILED DESCRIPTION OF INVENTION

In consequence, we, the present inventors, have found that when zinc cation is reacted in an inert organic solvent with an aminoglycosidic antibiotic which contains a deoxystreptamine moiety having a 3-aminoglycosyl or 3-alkylaminoglycosyl group linked to 6-hydroxyl group of the deoxystreptamine moiety and possibly having an aminoglycosyl group linked to 4-hydroxyl group of the deoxystreptamine moiety, zinc cation is complexed with and block amino-hydroxyl pairs locating at particular positions which may vary depending on the nature of the aminoglycosidic antibiotic; and that when the aminoglycosidic antibiotic-zinc cation complex so formed is reacted with an acylation reagent having an acyl group which is used conventionally for introduction of an amino-protecting group in the synthesis of polypeptides, this acylation reagent acylates at least one of such amino groups in the aminoglycosidic antibiotic which are not complexed with and hence not blocked by zinc cation, so that the amino group so acylated is protected; and also that when the resulting acylation product (ie., the aminoglycosidic antibiotic-zinc cation complex having the acylated amino group(s)) is treated with such a suitable reagent which will remove zinc cation from said acylation product, the zinc complex is destroyed, affording a selectively protected N-acylated derivative of the aminoglycosidic antibiotic of which the initially zinc-non-complexed amino group(s) has or have selectively been protected with the acyl group.

According to a first aspect of this invention, therefore, there is provided a process for the production of a selectively acylated N-protected derivative of an aminoglycosidic antibiotic, this aminoglycosidic antibiotic comprising a deoxystreptamine moiety having a 3-aminoglycosyl or 3-alkylaminoglycosyl group linked to 6-hydroxyl group of the deoxystreptamine moiety, and the selectively acylated N-protected derivative having some amino groups thereof selectively protected with an acyl group, which comprises the steps of:

(a) reacting an acylation reagent having an acyl group to be introduced as the amino-protecting group, with an aminoglycosidic antibiotic-zinc cation complex which has been formed by reaction of the aminoglycosidic antibiotic with a zinc salt in an inert organic solvent, to produce a complex of zinc cations with the selectively N-acylated derivative of the aminoglycosidic antibiotic having the initially non-complexed amino groups acylated, (b) and reacting the complex of zinc cations with the selectively N-acylated derivative of the aminoglycosidic antibiotic, with a reagent which removes zinc cations from said complex, to produce the desired selectively acylated N-protected derivative of the aminoglycosidic antibiotic.

The process according to this first aspect of the invention is useful to prepare such a selectively acylated N-protected derivative of an aminoglycosidic antibiotic by acylating some amino groups other than 1- and 3''-amino groups of the starting aminoglycosidic antibiotic, and such selectively N-protected derivative is useful in the chemical synthesis of 1-N-aminoacylated derivatives of aminoglycosidic antibiotics such as kanamycins, including amikacin ("Journal of Antibiotics" 25, 695–708 (1972)) which is proved in the recent years to be an effective antibacterial drug. These 1-N-aminoacylated derivatives of the aminoglycosidic antibiotics include those derived from a wide range of aminoglycosides such as kanamycin A, kanamycin B, kanamycin C, gentamicins, sisomicin and others as well as various deoxy-derivatives thereof, but all of them are common in that their 1-amino group is acylated with an α-hydroxy-ω-aminoalkanoyl group (see U.S. Pat. Nos. 3,781,268; 3,939,143; 3,940,382; and 4,001,208). By this 1-N-aminoacylation, the aminoglycosidic antibiotics are imparted with an antibacterial activity against such resistant bacterial to which the parent aminoglycosidic antibiotics are not active, and also the aminoglycosidic antibiotics are imparted with an improved antibacterial activity against a wider variety of strains of bacteria, as compared to the parent aminoglycosidic antibiotics.

We describe below more fully how to work the process of the first aspect of the invention.

The aminoglycosidic antibiotic which is to be reacted with zinc cation to form the zinc complex (which may also be termed as a zinc complex salt) according to this invention includes: such aminoglycosidic antibiotics comprising a deoxy-streptamine moiety of which 6-hydroxyl group is substituted by a 3-aminoglycosyl or 3-alkylaminoglycosyl group and of which 4-hydroxyl group may occasionally be substituted by an aminoglycosyl group. More particularly, the aminoglycosidic antibiotic available in this invention for formation of the zinc cation complex may be defined as such one comprising 6-O-(3''-amino- or 3''-alkylamino-3''-deoxyglycosyl)-2-deoxystreptamine optionally having a 4-O-(amino-glycosyl) group. Moreover, the aminoglycosidic antibiotic may be a 1-N-alkylaminoglycoside, like netilmicin. Examples of the aminoglycosidic antibiotics of the class available in this invention, there may be mentioned kanamycin A-group antibiotics including kanamycin A itself, 6'-N-alkylkanamycin A, particularly 6'-N-methylkanamycin A, 3'-deoxykanamycin A, 6'-N-methyl-3'-deoxykanamycin A, 4'-deoxykanamycin A, 6'-N-methyl-4'-deoxykanamycin A, 3',4'-dideoxykanamycin A (see Japanese Patent Application No. 11402/79) and 6''-deoxy- or 4'',6''-dideoxykanamycin A (see Japanese Patent Application No. 54733/79); kanamycin B-group antibiotics including kanamycin B itself, 3'-deoxykanamycin B (ie., tobramycin), 4'-deoxykanamycin B, 3',4'-dideoxykanamycin B (ie., dibekacin), 3',4'-dideoxy-3'-eno-kanamycin B, 6'-N-methyl-3',4'-dideoxykanamycin B; kanamycin C-group antibiotics including kanamycin C itself, 3'-deoxykanamycin C, 3',4'-dideoxykanamycin C; gentamicins A, B and C; verdamicin; sisomicin and netilmicin (ie, 1-N-ethylsisomicin) as well as the other known aminoglycosides. Of course, the process of the first aspect of the invention is applicable not only to such a new aminoglycosidic antibiotic which is not yet known at present and will be discovered in future, but also to new semi-synthetic aminoglycosidic antibiotic derivatives which will be produced in future by chemical transformation of known aminoglycosidic antibiotics.

Typical examples of the aminoglycosidic antibiotics to which the present invention is applicable include kanamycin A, kanamycin B, kanamycin C; and deoxy-derivatives of these kanamycins as well as 6'-N-alkyl derivatives thereof which are all represented by the following general formula (III):

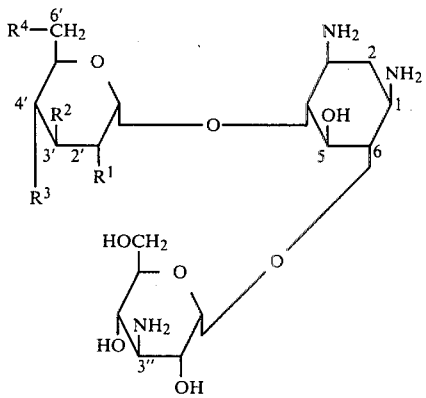

(III)

wherein $R^1$ is hydroxyl group or amino group, $R^2$ and $R^3$ are each hydrogen atom or hydroxyl group, and $R^4$ is hydroxyl group or amino group or an alkylamino group containing an alkyl of 1–4 carbon atoms, particularly methylamino group.

In order to form the aminoglycosidic antibiotic-zinc cation complex by reaction of the aminoglycosidic antibiotic with zinc cation in accordance with the invention, a particular aminoglycosidic antibiotic, either in the form of the free base or in the form of an acid-addition salt thereof, may be dissolved or suspended in an appropriate organic solvent or aqueous organic solvent, and to the resulting solution or suspension is added a suitable zinc salt in a quantity of at least 1 mol per mol of the aminoglycosidic antibiotic employed. Any ordinary organic solvent may be employed for this purpose, as far as the zinc complex formed after the addition of the zinc salt is at least partially soluble in it. However, use of a large volume of a polar organic solvent and particularly of greater volume of water should preferably be avoided, because the presence of polar organic solvent and water is likely to reduce the stability of the resulting aminoglycosidic antibiotic-zinc cation complex formed, so that the subsequent acylation reaction for introduction of the amino-protecting group is likely to give unsatisfactory result.

Thus, it is desirable to use an organic solvent of high solvent power such as dimethyl-sulfoxide for the solvent in which the zinc complex is to be formed, but it is feasible to employ aqueous dimethylsulfoxide, dimethylformamide, aqueous dimethylformamide, a mixture of dimethylsulfoxide and dimethylformamide, tetrahydrofuran, aqueous tetrahydrofuran, and even a lower alkanol such as methanol, ethanol and aqueous methanol.

Zinc cation may be supplied in the form of a zinc salt to the reaction system where the zinc complex is formed. Any zinc salt which is formed by reaction of zinc cation with an ordinary inorganic or organic acid may be used for the purpose of the present invention. In general, however, it is desirable to employ a zinc salt of a weak acid, such as zinc acetate, as it is usual that amongst the metal complexes containing amino group, a complex of non-quaternary amino group with a metal salt is more stable than a complex of an ammonium-type amine with a metal salt, and that the use of the zinc salt of a weak acid normally does not lead to formation of the relatively instable metal complex containing the ammonium-type amine. When the zinc salt of a strong acid, for example, zinc chloride is employed, the zinc complex as desired may be formed, too, but it is preferable to add a weakly alkaline salt such as sodium acetate, in addition to the zinc salt, for neutralization of the medium. Similarly, it is desirable to add an amount of sodium acetate or sodium hydroxide as a neutralizing agent when the starting aminoglycosidic antibiotic is used in the form of its acid-addition salt with a strong acid such as hydrochloric acid. In this case, however, care should be taken to avoid using unnecessarily excessive amount of the neutralizing agent, as otherwise zinc hydroxide would precipitate to disturb the formation of the complex. For instance, when an aminoglycosidic antibiotic tetra-hydrochloride is used for the complexing, 4 mol of sodium hydroxide should preferably be added to neutralize the reaction mixture.

As long as the total molar quantity of zinc salt used is at least equal to the molar quantity of the aminoglycosidic antibiotic, the complexing reaction may proceed. However, it is preferable to use the zinc salt in a quantity of substantially more than 1 mol per mol of the aminoglycosidic antibiotic, so that the equilibrium of the complexing reaction is shifted in favor of the formation of the complex. Favorable yield of the zinc complex may be obtained when using the zinc salt in a quantity of about 2.3–6 mol per mol of the aminoglycoside, but in practice it is most preferable to use the zinc salt in a quantity of 4–5 mol per mol of the aminoglycoside. Time required for complete complexing reaction after the addition of the zinc salt may vary depending on the nature of the organic solvent used, and it may be in the range of "instantaneously" (when using aqueous organic solvent) to 20 hours. The complexing reaction normally may proceed at ambient temperature, but heating or cooling may be done.

In this way, a solution or suspension containing the zinc complex of the aminoglycosidic antibiotic is prepared, to which is then added an acylation reagent having an acyl group to be introduced as the amino-protecting group.

The acylation reagent employed according to this invention may be a usual amino-protecting reagent, and this is used to ensure that the free, non-complexed amino groups in the resultant aminoglycosidic antibiotic-zinc cation complex are acylated by and blocked with the acyl group of the acylation reagent. The acyl group may be an alkanoyl group, an aroyl group, an alkoxycarbonyl group, an aralkyloxycarbonyl group, an aryloxycarbonyl group, an alkylsulfonyl group, an aralkylsulfonyl group or an arylsulfonyl group which are all the conventional amino-protecting group. The acylation reagent available for this purpose may either be a carboxylic acid of the following general formula (IVa):

$$R^5COOH \qquad (IVa)$$

wherein $R^5$ is hydrogen, an alkyl group, particularly an alkyl group of 1–6 carbon atoms, an aryl group, particularly phenyl, or an aralkyl group, especially benzyl, and these groups being occasionally further substituted, or an acid halide, acid anhydride or active ester of said carboxylic acid (IVa); or a chloroformate of the following general formula (IVb):

$$R^5O\text{-}CO\text{-}Cl \qquad (IVb)$$

or a p-nitrophenyl carbonate of the following general formula (IVc):

$$R^5O\text{-}CO\text{-}O\text{-}C_6H_5\text{-}p\text{-}NO_2 \qquad (IVc)$$

or active N-hydroxysuccinimide ester of the following formula (IVd):

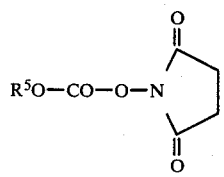
(IVd)

or an azidoformate of the following formula (IVe):

$$R^5O-CO-N_3 \quad (IVe)$$

where $R^5$ is as defined above; or a sulfonic acid of the following general formula (IVf):

$$R^6SO_3H \quad (IVf)$$

wherein $R^6$ is a hydrogen, an alkyl group, especially an alkyl group of 1-6 carbon atoms, an aryl group, particularly phenyl, or an aralkyl group, especially a phenylalkyl group such as benzyl, and these groups being occasionally further substituted, or an acid halide, acid anhydride or active ester of said sulfonic acid. Accordingly, it is evident that the acylation reaction for protection of amino groups according to this invention is an acylation of a broad meaning, including, for example, formylation, acetylation, propionylation, trifluoroacetylation, benzyloxycarbonylation, p-methoxybenzyloxycarbonylation, t-butoxycarbonylation, phenoxycarbonylation, tosylation, mesylation and other equivalent ones.

Particular examples of the available acylation reagent include acetoxyformyl, p-nitrophenyl formate, acetic anhydride, acetyl chloride, propionic anhydride, p-nitrophenol ester of trifluoroacetic acid, trifluoroacetic acid ester, N-benzyloxycarbonyloxysuccinimide (a representative active ester), N-benzyloxycarbonyloxyphthalimide, benzyloxycarbonyl chloride, p-methoxybenzyloxycarbonyloxy-p-nitrophenyl, t-butoxycarbonylazide, phenoxycarbonyl chloride, tosyl chloride, mesyl chloride and others.

The acylation reagent, either as such or as a solution in a solvent such as tetrahydrofuran and dimethylsulfoxide or in a mixture of these solvents, may be added to the solution or suspension containing the aminoglycosidic antibiotic-zinc complex. The molar quantity of the acylation reagent added may usually be equal to or a little excessive than the number of the non-complexed amino groups with which the acylation reagent is to react. In some cases, however, the molar quantity of the acylation reagent added may be up to a molar quantity of about 3 times higher than the number of the non-complexed amino groups. The acylation reagent may be added either at once or in portions slowly over a duration of 2-3 hours, though it may usually be added over a time of 30 minutes to 1 hour. The acylation may be conducted at a temperature of $-20°$ C. to $100°$ C. but may normally be effected at a temperature ranging from $0°$ C. to ambient temperature. In some cases, the reaction temperature may be kept low at the time of addition of the acylation reagent and be then elevated gradually as the acylation proceeds. Normally, the acylation reaction may be effected in situ in the organic solvent in which the aminoglycosidic antibiotic-zinc cation complex was formed. This acylation of the zinc complex produces the N-acylated zinc complex, that is, the complex of zinc cations with the selectively N-acylated aminoglycosidic antibiotic derivative.

According to the process of the first aspect of the invention, the step of the acylation of the aminoglycosidic antibiotic-zinc cation complex is followed by the step of removing zinc cation from the N-acylated zinc complex (namely, destroying of the zinc complex) to yield the selectively protected N-acylated derivative of the aminoglycosidic antibiotic which is free from zinc cations.

For removal of zinc cation from the N-acylated zinc complex, it is necessary to treat the N-acylated zinc complex with a suitable reagent which removes zinc cation from said N-acylated zinc complex. For this purpose, there are many available methods. The first method is to react a zinc-precipitating agent, which is capable of converting zinc cation into a water-insoluble zinc compound such as zinc sulfide, zinc hydroxide or zinc carbonate while the N-acylated zinc complex is still remaining dissolved in the acylation reaction mixture where the aminoglycosidic antibiotic-zinc cation complex has been acylated, or after it is transferred into a new solution in a fresh volume of an organic solvent from said acylation reaction mixture.

The zinc-precipitating agent available in the first method include hydrogen sulfide, an alkali metal sulfide such as sodium sulfide, ammonium sulfide, an alkaline earth metal sulfide such as calcium sulfide and an alkali metal carbonate such as sodium carbonate or ammonium hydroxide. In some cases, the removal of zinc cations from the N-acylated zinc complex may be effected merely by addition of water. According to this first method, addition of the zinc-precipitating agent to the solution of the N-acylated zinc complex brings about a comparatively rapid precipitation of insoluble zinc compound formed from zinc cations, and the precipitate may be removed out by filtration. The N-acylated aminoglycosidic antibiotic derivative which then remain in the filtrate solution may be recovered by concentration of the solution or by extraction from the solution, and if necessary, may be purified subsequently. For purification, for example, column chromatography with silica gel is useful. A second method is (i) to concentrate or concentrate to dryness by evaporation of the solvent or (ii) to dilute with a liquid diluent the aforesaid acylation reaction mixture or the new solution of the N-acylated zinc complex transferred into the fresh volume of the organic solvent so as to give an oily or solid deposit, concentrate or residue, followed by recovering the desired N-acylated aminoglycosidic antibiotic derivative from said deposit, concentrate or residue in any way. The liquid diluent available in this second method is water or a such an organic liquid in which the N-acylated zinc complex as the whole or the N-acylated aminoglycosidic antibiotic derivative moiety of said N-acylated zinc complex has no or little solubility.

According to the aforesaid second method, at first, the acylation reaction mixture containing the N-acylated zinc complex (or the new solution of the N-acylated zinc complex transferred into an organic solvent) is concentrated or concentrated to dryness to give the oily or solid deposit or residue. When a hardly vaporisable organic solvent such as demethylsulfoxide etc., was employed as the reaction medium for the N-acylation of the zinc complex, it is possible that the acylation reaction mixture containing the N-acylated zinc complex is admixed with a diluent organic liquid such as ethylether so that the hardly vaporisable organic solvent medium is dissolved in (or diluted with) the diluent, whereby a solid or an oil comprising the N-acylated zinc complex is deposited therefrom. In these ways, an oily or solid deposit or residue is obtained, which is normally a mixture composed of (i) the N-acylated zinc complex, that is, the complex of zinc cations with the N-acylated aminoglycosidic antibiotic derivative, (ii) the N-acylated aminoglycosidic antibiotic derivative liberated by destroying of the complexing association in a portion of the N-acylated zinc complex due to the substantial absence of the organic solvent medium, (iii) an amount of the inorganic zinc salt formed by the destroying of the complexing association in the portion of the N-acylated zinc complex, (iv) an amount of the zinc salt which was added initially as an excess and remaining unreacted in the complexing reaction, and possibly (v) some residual amount of the organic solvent employed in the preceding operations.

The above oily or solid deposit or residue (the aforesaid mixture) may subsequently be treated by either of the procedures (a), (b) and (c) stated hereinunder.

(a) The oily or solid deposit or residue (the aforesaid mixture) is admixed with water or such a kind of a polar organic solvent, an aqueous polar organic solvent or mixed polar organic solvents which is polar organic liquid(s) having the effect of destroying the complexing association of zinc cations in the N-acylated zinc complex present in said deposit or residue and in which amounts of the zinc salt liberated and initially present unreacted are soluble but the desired N-acylated aminoglycosidic antibiotic derivative is insoluble. In this way, the N-acylated zinc complex is destroyed to liberate the zinc cations therefrom, to allow the zinc cations to be dissolved in and extracted out as the zinc salt with the water or (aqueous) organic solvent(s) and to leave the desired N-acylated aminoglycosidic antibiotic derivative as an insoluble residue to be recovered. This residue may optionally be purified by re-dissolution in an organic solvent. The polar organic solvent available in this procedure (a) includes, for example, methanol, ethanol, liquid ammonia, ethylamine and triethylamine. These polar organic solvents and water serve as the zinc cation-removing reagent, accordingly.

(b) Alternatively, the oily or solid deposit or residue (the aforesaid mixture) is admixed with such another kind of polar organic solvent, either anhydrous or aqueous, which has the effect of destroying the complexing association of zinc cations in the N-acylated zinc complex present in said deposit or residue and in which the liberated zinc salt is not soluble but the desired N-acylated aminoglycosidic antibiotic derivative is soluble, whereby the N-acylated zinc complex is destroyed to liberate the N-acylated aminoglycosidic antibiotic derivative therefrom and to allow the latter to be dissolved in and extracted out with said polar organic solvent and hence to be separated from the zinc salt which is liberated but remaining not dissolved in said polar organic solvent. In this way, the solution of the desired N-acylated aminoglycosidic antibiotic derivative in the polar organic solvent is recovered and, if desired, may be purified eg. chromatographically, followed by concentration of the purified solution for isolation of the desired N-acylated product.

(c) Further alternatively, the oily or solid deposit or residue (the aforesaid mixture) as obtained in the above-mentioned second method may be again dissolved as the whole in a suitable organic solvent containing a proportion of water, if the whole deposit or residue is soluble or substantially soluble in water. The solution so obtained may then be subjected to a chromatographic procedure during which the liberated zinc salt and the liberated N-acylated aminoglycosidic antibiotic derivative can be recovered separately from the solution. We have found that for this chromatographic procedure are useful various kinds of cation-exchange resins, anion-exchange resins, chelate-exchange resin and water-insoluble high-polymers containing functional groups capable of combining with a metal, such as chitin or chitosan. The available grades of cation-exchange resin for this purpose include ones containing carboxyl groups (—COOH) as the exchange functions, and ones containing sulfonyl groups (—$SO_3H$) as the exchange functions. When using an cation-exchange resin containing carboxylic functions for the above-mentioned chromatographic procedure, the aforesaid oily or solid deposit or residue (the aforesaid mixture) is dissolved in a suitable aqueous organic solvent, for example, a mixture of water and methanol containing optionally 10% to 90% by volume of water or a mixture of water and dioxane containing optionally 10% to 90% by volume of water, and the resulting solution is charged into a column of said cation-exchange resin. The column is then washed well with a further amount of the above-mentioned aqueous organic solvent, followed by the development using as the eluent an amount of the above-mentioned aqueous organic solvent containing further a quantity of an acid or a base. As this acid may be used a weak organic acid such as acetic acid, or a diluted inorganic acid such as dilute hydrochloric acid. As the base may be used ammonium hydroxide for almost cases. The concentration of the acid or base in the developing solvent (the eluent) may suitably be 0.01% to 5% by weight of the developing solvent. The desired N-acylated aminoglycosidic antibiotic derivative can be separated from the complexing zinc cations during the process of the development, because the cation-exchange resin used exerts different adsorptive affinities against the desired N-acylated aminoglycoside and the zinc cations so that the force of the former to be associated with the resin is different from the force of the latter to be associated with the resin. In this way, the elute can be collected in fractions so as to give fractions containing the desired N-acylated aminoglycoside free from the zinc salt, which may then be concentrated to afford the desired aminoglycosidic antibiotic N-acylated derivative.

When using a cation-exchange resin containing sulfonyl functions for the above chromatographic procedure, the separation and recovery of the desired N-acylated aminoglycosidic antibiotic derivative may be achieved in the same way as in the above case, because entirely the same mechanism is involved in the separation of the N-acylated aminoglycoside from the complexing zinc cations. On the other hand, when using a weakly or strongly basic anion-exchange resin for the chromatographic procedure, the portion of the N-acylated aminoglycoside in the N-acylated zinc complex which is containing one or more non-acylated amino group(s) therein is normally not be adsorbed by the weakly or strongly basic anion-exchange resin owing to the ionic repellance between them, so that the development of the anion-exchange resin column with a suitable aqueous organic solvent permits the N-acylated aminoglycosidic antibiotic derivative to be eluted from the column while the zinc cations remain in the column.

When the chromatographic procedure is conducted using a chelate-exchange resin which is able to combine with zinc cations by the metal-chelating ability of this resin, a solution of the aforesaid oily or solid deposit or residue (the aforesaid mixture) in an aqueous organic solvent is charged in a column of chelate-exchange resin, which is then developed with a suitable development solvent to allow the desired N-acylated aminoglycoside to be eluted preferentially out of the column, while the zinc cations remain bounded in the chelate-exchange resin. The water-insoluble high-polymer containing the functions capable of combining with a metal, for example, chitin and chitosan, may be employed in the same manner as when using the chelate-exchange resin.

(d) Moreover, a third method is possible, in which the aforesaid acylation reaction mixture in which the acylation of the zinc complex for protection of the amino groups was conducted is directly charged into a column of a cation- or anion-exchange resin, chelate-exchange resin, or a water-insoluble high-polymer containing the metal-combining functions, so that the N-acylated zinc complex is adsorbed by the resin or high-polymer. The column may then be washed with an aqueous organic solvent, if necessary, and may subsequently developed with an aqueous organic solvent containing or not containing an acid or a base as mentioned in the above procedure (c), followed by similar operations to those of the procedure (c), whereby the removal of zinc cations from the N-acylated zinc complex as well as the recovery of the desired N-acylated aminoglycosidic antibiotic derivative are achieved.

(e) Furthermore, a fourth method is also possible for the recovery of the desired N-acylated aminoglycosidic antibiotic derivative, in which method the aforesaid acylation reaction mixture containing the N-acylated zinc complex is treated immediately with water by admixing with water, in case the desired N-acylated aminoglycosidic antibiotic derivative itself is insoluble or substantially insoluble in water. 3,2',6'-Tri-N-benzyloxycarbonyldibekacin may be mentioned as an examples of the N-acylated aminoglycosidic antibiotic derivative which is substantially insoluble in water. In this case, when the acylation reaction mixture containing the N-acylated zinc complex comprising a substantially water-insoluble N-acylated aminoglycoside derivative is immediately admixed with water, the zinc-complexing association in the N-acylated zinc complex is broken to allow the water-insoluble N-acylated aminoglycoside derivative to be precipitated as a solid, while the zinc salt formed from the liberated zinc cations remains in solution, whereby the desired N-acylated aminoglycosidic antibiotic derivative as a substantially pure product can be recovered separately from the zinc salt.

As be stated in the above, the N-acylation, namely the amino-protecting reaction is conducted with the zinc complex of the aminoglycosidic antibiotic in accordance with the process of the first aspect invention, and the complex of zinc cations with the mono-, di-, tri- or poly-N-acylated aminoglycoside derivative so formed is such one in which the zinc cations used are complex-associated with the structure of the N-acylated aminoglycoside derivative. Therefore, when the desired N-acylated aminoglycoside derivative is insoluble or sparingly soluble in water, a simple operation of admixing water with the acylation reaction mixture containing the N-acylated zinc complex causes the water-insoluble N-acylated aminoglycoside derivative to be precipitated as a solid while the liberated zinc cations are removed therefrom by dissolution in the water (as in the case of the fourth method described in the preceding paragraph (e)). The water-insoluble precipitate so obtained may immediately be employed as an initial material for subsequent reactions for semi-synthetic production of a desired final product. More generically, however, the N-acylated aminoglycosidic antibiotic derivative itself is often soluble in water or partly soluble in water, and hence the desired N-acylated aminoglycoside derivative can be recovered only in a considerably lowered yield if the simple treatment of admixing water immediately with the acylation reaction mixture is adopted. For these reasons, better result may rather be obtained when applying either one of the above-mentioned procedures (b) and (c) in which the N-acylated zinc complex (that is, the complex of zinc cations with the N-acylated aminoglycosidic antibiotic derivative formed from the N-acylation reaction) is at first separated from the acylation reaction mixture, the N-acylated zinc complex so separated is then dissolved in water or an aqueous organic solvent and the resulting solution is further processed for removal of zinc cations therefrom. Meanwhile, one of the simple methods of removing zinc cations which are generally obvious is such one in which hydrogen sulfide or an alkali sulfide is reacted as a precipitating agent with zinc cations to precipitate the latter as zinc sulfide (as one mode of the first method set forth in the above paragraph (a)). However, zinc sulfide often precipitates as colloidal deposit which is difficult to be filtered out, and besides, hydrogen sulfide and an alkali sulfide have objectionable odor and are not suitable for use in commercial working of the process. Thus, we have made our extensive research in an attempt to provide a practical method of removing zinc cations from the zinc complex without resorting on the use of a sulfide, and now we have succeeded in developing the efficient and facile methods of removing zinc cations by using the above-mentioned exchange resins or other polymeric material (as in the case of the procedures (c) and (d)). These procedures (c) and (d) are commercially very much advantageous and valuable as they are easy to operate, give high efficiency of the separation of zinc cations and provide a high yield of the desired N-acylated aminoglycosidic antibiotic derivative.

After all, the above described various methods and procedures of treating the N-acylated zinc complex with the zinc cation-removing reagent may be summarized as follows:

(i) The complex of zinc cations with the selectively N-acylated aminoglycosidic antibiotic derivative is once separated from the acylation reaction mixture before it is reacted with a reagent of removing zinc cations from this complex.

(ii) The complex of zinc cations with the selectively N-acylated aminoglycosidic antibiotic derivative is separated from the acylation reaction mixture by extraction with an organic solvent, by evaporating the organic solvent medium from the acylation reaction mixture or by diluting the acylation reaction mixture with a diluent organic solvent, before it is reacted with a reagent of removing zinc cations.

(iii) The complex of zinc cations with the selectively N-acylated aminoglycosidic antibiotic drivative once separated is admixed with water or a polar organic solvent, either anhydrous or aqueous, which serves as the zinc cation-removing reagent. This polar organic solvent is either such one in which the zinc salt is soluble but in which the N-acylated aminoglycosidic antibiotic derivative is insoluble, or such one in which the zinc salt is insoluble but in which the N-acylated aminoglycosidic antibiotic derivative is soluble.

(iv) The complex of zinc cations with the N-acylated aminoglycosidic antibiotic derivative once separated is again dissolved wholly in an organic solvent containing a proportion of water, and the resulting solution is subjected to a chromatographic procedure using a cation-exchange resin, an anion-exchange resin, chelate-exchange resin or a water-insoluble polymer containing functional groups capable of combining with a metal, which serves as the zinc cation-removing reagent.

(v) The acylation reaction mixture is directly passed through a column of a cation-exchange resin, an anion-exchange resin, chelate-exchange resin or a water-insoluble polymer containing the metal-combining functions for adsorption of the complex of zinc cations with the N-acylated aminoglycosidic antibiotic derivative, and the column is then developed with an aqueous organic solvent containing or not containing an amount of acid or base, and the eluate is collected in fractions, followed by recovery of the fractions containing the desired selectively N-acylated aminoglycosidic antibiotic derivative but containing no zinc cations.

(vi) When the desired N-acylated aminoglycosidic antibiotic derivative is insoluble or substantially insoluble in water, the acylation reaction mixture is immediately admixed with water, so that said derivative is precipitated separately from the zinc salt remaining dissolved in water.

(vii) The acylation reaction mixture is immediately treated with hydrogen sulfide, an alkali metal sulfide or an alkaline earth metal sulfide which precipitates zinc cations as zinc sulfide, or with ammonium hydroxide which precipitates zinc cations as zinc hydroxide.

In the zinc complex involved in the process of the first aspect invention, zinc cations are principally complexing with 1-amino and 3''-amino groups of the aminoglycosidic antibiotic, and hence the N-acylation of the aminoglycosidic antibiotic-zinc cation complex followed by the removal of zinc cations therefrom normally gives the N-acylated aminoglycosidic antibiotic derivative in which amino and/or alkylamino groups other than 1-amino and 3''-amino groups are protected by the acyl group. When the N-acylated aminoglycosidic antibiotic derivative so obtained from the process of the first aspect invention is then 1-N-acylated with an α-hydroxy-ω-aminoalkanoic acid in a known manner as set forth in the aforesaid U.S. Pat. Nos. 3,781,268 and 3,939,143, for instance, followed by removal of the residual amino-protecting groups from the resultant 1-N-acylated product, there is afforded a semi-synthetic 1-N-acylated aminoglycosidic antibiotic which is known as a useful antibacterial agent.

Synthesis of the 1-N-acylated aminoglycosidic antibiotics is now described with reference to an illustrative use of kanamycin A as a starting material. When kanamycin A is used as the initial material in the process of the first aspect invention, 1-amino and 3''-amino groups of kanamycin A are initially blocked by complexing with zinc cations upon the formation of its zinc complex. Accordingly, when the kanamycin A-zinc cation complex is acylated with a suitable acylation reagent according to the invention or with another kind of amino-blocking agent, the non-complexed 3-amino and 6'-amino groups of the kanamycin A molecule can be protected by the acyl group of the acylation reagent employed or by the other kind of amino-blocking group. After subsequent removal of the complexing zinc cations from the N-acylated kanamycin A-zinc cation complex, the resulting N-acylated kanamycin A derivative is reacted with an acylating agent having an acyl group to be introduced into 1-amino group of the kanamycin A molecule. Then, this acyl group reacts only with the unblocked 1-amino and 3''-amino groups of kanamycin A. At this time, 1-amino group is normally a little more reactive than 3''-amino group, so that the desired 1-N-acylated kanamycin A derivative may be obtained in a little higher yield than the 3''-N-acylated kanamycin A derivative. Subsequent N-deprotection of the 1-N-acylated kanamycin A derivative so obtained affords the 1-N-acylated kanamycin A as the final desired product. Therefore, when utilizing the process of the first aspect invention, it will be obvious that the desired 1-N-acylkanamycin A can be obtained in a higher yield, as compared to when unprotected kanamycin A or 6'-N-protected kanamycin A is immediately reacted with an acylating agent for the purpose of 1-N-acylation of kanamycin A. If a kanamycin without any N-protection is reacted with a 1-N-acylating agent, it is found that there are formed the mixed N-acylated products containing a very small proportion (usually 1% to a few %) of the desired 1-N-acylated product.

In case the process of the first aspect invention is applied to a kanamycin of the aforesaid general formula (III), some or all of the amino groups other than 1- and 3''-amino groups of that kanamycin used are protected to give an N-acylated kanamycin derivative represented by the following general formula (V):

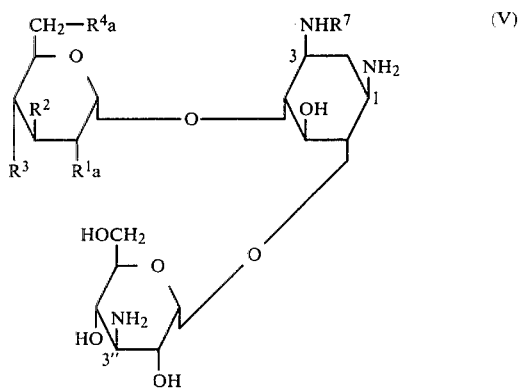

wherein $R^1a$ is hydroxyl group, amino group ($-NH_2$), a group $-NHCOR^5$, or a group $-NHCO.OR^5$ or a group $-NHSO_2R^6$; $R^4a$ is hydroxyl group, a group $-NHCOR^5$, a group

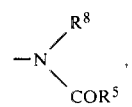

a group $-NHCO.OR^5$, a group

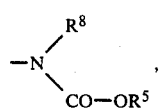

a group —NHSO$_2$R$^6$ or a group

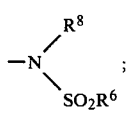

R$^2$ and R$^3$ are each as defined in the general formula (III); R$^7$ is a group —COR$^5$, a group —CO.OR$^5$ or a group —SO$_2$R$^6$; R$^5$ and R$^6$ are as defined in the formulae (IVa) to (IVf); and R$^8$ is alkyl group, especially of 1–4 carbon atoms.

Thus, in case the process of the first aspect invention is applied to a kanamycin, there is usually obtained an N-protected kanamycin derivative of the formula (V) in which all the amino groups other than the amino and/or alkylamino groups present at the 1- and 3″-positions of the kanamycin molecule are blocked. Nonetheless, if the acyl group to be introduced as the amino-blocking group is relatively large in its steric size, for example, with t-butoxycarbonyl group, or if the molar quantity of the acylation reagent used is less than the quantity stoichiometrically required to acylate all the non-complexed amino groups of the kanamycin molecule even though the acyl group of the acylation reagent employed is of an ordinary size, or if the acylation reaction is stopped at an intermediate stage, there is obtained such an N-protected kanamycin derivative in which the number of the acylated amino groups in the kanamycin molecule is less than in the above case, and then in particular cases there is obtained such a limitedly N-acylated kanamycin derivative in which 6′-amino or 6′-alkylamino group is exclusively acylated, owing to that 6′-amino or 6′-alkylamino group is more reactive than the other amino groups in the kanamycin molecule.

The N-acylated kanamycin derivative of the general formula (V) is an important intermediate useful in the semisynthetic production of various kinds of kanamycin derivatives. The compound of the formula (V) has an increased value as an intermediate material for chemical synthesis, for instance, particularly when it is involved in a process of producing semi-synthetic 1-N-acylated aminoglycosidic antibiotics active against the kanamycin-resistant bacteria, by acylating 1-amino group of the compound (V) with an α-hydroxyl-ω-aminoalkanoic acid and then removing the protective groups from the blocked amino and/or alkylamino groups of the resulting 1-N-acylation product.

As an instance, when the intermediate compound (V) is to be acylated with an acyl group, eg., with (S)-4-benzyloxycarbonylamino-2-hydroxybutyryl group, the compound (V) may be reacted in a suitable organic solvent such as aqueous tetrahydrofuran with a correspondingly substituted butyric acid or its equivalent reactive derivative such as an active ester, for example, N-hydroxysuccinimide ester, N-hydroxyphthalimide ester or p-nitrophenol ester, whereby the 1-N-acylation product is formed. Subsequently, removal of the benzyloxycarbonyl group and the protective group (R$^7$) in the formula (V) from the 1-N-acylation product may be effected by a conventional N-deprotecting technique, eg., either by hydrolysis with acid or base, or by reduction with reducing metal, or by catalytic hydrogenolysis with hydrogen, or by radical reduction with sodium in liquid ammonia, to give a semi-synthetic kanamycin derivative having (S)-4-amino-2-hydroxybutyryl group bounded with 1-amino group of kanamycin which is active against the resistant bacteria and is represented by the following general formula (VI):

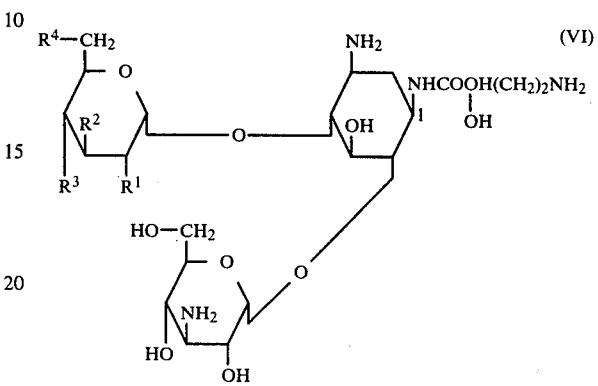

wherein R$^1$, R$^2$, R$^3$ and R$^4$ each have the same meanings as defined in the formula (III). In the above process, generally, an N-protected derivative of an α-hydroxyl-ω-aminoalkanoic acid of the formula (VII):

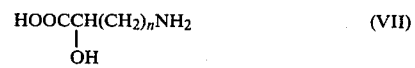

wherein n is an integer of 1, 2 or 3 may be employed instead of the (S)-4-benzyloxycarbonylamino-2-hydroxybutyric acid, to give a 1-N-((S)-α-hydroxy-ω-aminoalkanoyl)kanamycin derivative.

Furthermore, the invention includes further a process for the production of a selectively protected N-acylated derivative of an aminoglycosidic antibiotic comprising a 6-O-(3″-amino- or 3″-alkylamino-3″-deoxyglycosyl)-2-deoxystreptamine moiety possibly having a 4-O-(aminoglycosyl) group in which derivative all the amino groups (including 3″-amino group) other than 1-amino group of the aminoglycoside molecule are blocked or protected by same or different acyl groups.

According to the process of the first aspect invention (hereinafter sometimes called "zinc-complexing" process), it is feasible to prepare such a selectively but partially protected N-acylated derivative of the aminoglycosidic antibiotic in which derivative all the amino groups other than the two, 1-amino and 3″-amino (or 3″-alkylamino) groups of the aminoglycoside molecule are protected by an acyl group and hence 1-amino and 3″-amino (or 3″-alkylamino) groups are remaining unprotected. Even when this partially protected N-acylated aminoglycosidic antibiotic derivative is reacted with an α-hydroxy-ω-aminoalkanoic acid or its reactive equivalent for the purpose of effecting the 1-N-acylation as mentioned above, it is actual that there are yielded mixed acylation products comprising (i) the 1-N-acylated product where only 1-amino group of the aminoglycoside molecule has been acylated with the α-hydroxy-ω-aminoalkanoic acid, (ii) the 3″-N-acylated product where only 3″-amino (or 3″-alkylamino) group has been acylated, (iii) both 1-amino and 3″-amino (or 3″-alkylamino) groups have been acylated, and (iv) the unreacted material where none of 1- and 3''-amino (or 3''-alkylamino) groups have been acylated. In order to obtain the ultimately desired 1-N-acylation product from the above mixed acylation products, therefore, it is always necessary to carry out an additional step in which the 1-N-acylation product is isolated therefrom by chromatography or by any other isolation method. As the 1-amino group is fortunately more reactive than the 3''-amino (or 3''-alkylamino) group, actual yield of the desired 1-N-acylation product usually is about 40% to 60% and exceeds a theoretically maximum yield of 25% which would be calculated with assuming that the reactivity of 1- and 3''-amino (or 3''-alkylamino) groups should be entirely equal to each other. Nonetheless, even if the reaction conditions for the 1-N-acylation are adjusted to best ones, it is inevitable that the undesirably N-acylated products are by-formed, and always it needs an additional step to remove the undesired N-acylated by-products by subjecting the mixed acylated products carefully to a column chromatography.

In order to eliminate this disadvantage, it is obviously required to prepare such a selectively protected N-acylated derivative of the aminoglycosidic antibiotic in which all the amino groups other than 1-amino group have been protected. In order to meet this requirement, we have made further research in an attempt to provide a process which is able to selectively protect 3''-amino (or 3''-alkylamino) group of the selectively but partially protected N-acylated aminoglycosidic antibiotic derivative containing free 1- and 3''-amino groups as obtained from the above-described "zinc-complexing" process, while 1-amino group is remaining unblocked.

As a result, we have now succeeded to find out that when the partially protected N-acylated aminoglycosidic antibiotic derivative as obtained from the "zinc-complexing" process is reacted with an acylating agent selected from formic acid esters, dihalo- or trihalo-alkanoic acid esters, N-formylimidazole, 3''-amino or 3''-alkylamino group can preferentially be acylated for the blocking purpose without acylating 1-amino group. This selective 3''-N-protecting process may be combined with the above-described "zinc-complexing" process (ie., the process of the first aspect invention) so that there is produced in a facile and efficient way such a selectively protected N-acylated derivative of the aminoglycosidic antibiotic comprising a 6-O-(3''-amino- or 3''-alkylamino-3''-deoxyglycosyl)-2-deoxystreptamine moiety in which derivative all the amino groups other than 1-amino group of the aminoglycoside molecule have been protected selectively with same or different acyl groups. In the combination of the "zinc-complexing" process with the selective 3''-N-protecting process, an advantage is obtained that the ultimately desired 1-N-unprotected but other N-fully-protected derivative of the aminoglycosidic antibiotic can be produced from the parent aminoglycosidic antibiotic material in an overall yield of 70% or more. When this 1-N-unprotected but other N-fully-protected derivative is employed for the 1-N-acylation of the aminoglycosidic antibiotic, there is provided a further advantage that the undesirably N-acylated products are substantially not by-formed, so that recovery and purification of the desired 1-N-acylation product is very facilitated.

According to the second aspect of this invention, therefore, there is provided a process for the production of a selectively protected N-acylated derivative of an aminoglycosidic antibiotic comprising a 6-O-(3''-amino- or 3''-alkylamino-3''-deoxyglycosyl)-2-deoxystreptamine moiety optionally having a 4-O-(aminoglycosyl) group in which derivative 1-amino group of the deoxystreptamine moiety is unprotected but all the other amino groups in the aminoglycoside molecule are protected with same or different acyl groups; the process comprising a step of:

(a) reacting an alkanoic acid ester of the formula (VIII):

wherein $R^a$ is a hydrogen atom or a dihaloalkyl or trihaloalkyl group of 1-6 carbon atoms, and $R^b$ is an alkyloxy group of 1-6 carbon atoms, an aralkyloxy group, especially benzyloxy group, an aryloxy group, especially phenyloxy group, or an N-formylimidazole as the acylating agent in an inert organic solvent with a partially protected N-acylated derivative of the aminoglycosidic antibiotic in which 1-amino and 3''-amino or 3''-alkylamino groups are unprotected and all the other amino groups are protected with an acyl group as the amino-protecting group, to effect selective acylation of 3''-amino or 3''-alkylamino group of the partially protected N-acylated derivative with the acyl group $R^aCO-$ of said acylating agent and thereby give the desired 1-N-unprotected and other N-fully-protected derivative of the aminoglycosidic antibiotic.

The aminoglycosidic antibiotics which are available in the process according to the second aspect of this invention are the same as these available in the process of the first aspect invention and mentioned hereinbefore.

Embodiments of the process according to the second aspect of the invention are now described more fully.

The partially protected N-acylated aminoglycosidic antibiotic derivative which is to be reacted with the acylating agent of the formula (VIII) according to the second aspect of the invention and of which all the amino groups other than 1-amino and 3''-amino (or 3''-alkylamino) groups in the aminoglycoside molecule are protected may be such one which is produced the aforesaid "zinc-complexing" process according to the first aspect invention. Accordingly, the acyl group originally present in the partially protected N-acylated aminoglycosidic antibiotic derivative used in the second aspect invention is the same as the acyl group ($R^5CO-$, $R^5OCO-$ or $R^6SO_2-$ group in the formula IV$_{a-e}$) of the acylation reagent employed in the first aspect invention and generally may be an alkanoyl group, an aroyl group, an alkoxycarbonyl group, an aralkyloxycarbonyl group, an aryloxycarbonyl group, an alkylsulfonyl group, an aralkylsulfonyl group or an arylsulfonyl group known as the conventional amino-protecting group. Moreover, the partially protected N-acylated aminoglycosidic antibiotic derivative employed as the starting material may also be such one which has been prepared by the aforesaid Nagabhushan et al's method according to U.S. Pat. No. 4,136,254.

In carrying out the process of the second aspect invention, the partially protected N-acylated aminoglycosidic antibiotic derivative having the unprotected 1- and 3''-amino (or 3''-alkylamino) groups is used as the starting material and is dissolved or suspended in an appropriate inert organic solvent. To the resulting solution or suspension is added an alkanoic acid ester of the formula (VIII) or N-formylimidazole as the acylating agent in an amount which is at least equimolar to the starting material used. The inert organic solvent may preferably be such one which shows a high dissolution power for the starting material, for example, dimethylsulfoxide, dimethylformamide and hexamethylphosphoric triamide, but it is possible to use tetrahydrofuran, dioxane, acetonitrile, nitromethane, sulfolane, dimethylacetamide, chloroform, dichloromethane, methanol, ethanol, n-butanol and t-butanol, as well as aqueous ones of these solvents. Benzene, toluene and ethylether may be used as the reaction medium solvent, though these are not very suitable as these bring about poorer yield of the desired product. With the acylating agent of the formula (VIII), $R^a$ may preferably be a dihaloalkyl or trihaloalkyl group, particularly dichloromethyl, trifluoromethyl or trichloromethyl, and $R^b$ may preferably be an alkyloxy group such as methoxy or ethoxy. When $R^b$ is an aryloxy group, it may be phenoxy. Particular examples of the acylating agent (VIII) include methyl formate, ethyl formate, butyl formate, benzyl formate, phenyl formate, methyl dichloroacetate, methyl trichloroacetate, phenyl trichloroacetate, methyl trifluoroacetate, ethyl trifluoroacetate and phenyl trifluoroacetate. Using this class of the acylating agent, 3″-amino group of the starting material can preferentially be formylated, dichloroacetylated, trichloroacetylated or trifluoroacetylated. Trifluoroacetic acid ester, especially ethyl trifluoroacetate is most preferred. This class of the acyl group is advantageous in that it is very easily removable in the subsequent N-deprotecting step by a conventional deprotection method. If the alkanoic acid alkyl ester of the formula (VIII) is not employed as the acylating agent but in stead thereof a corresponding alkanoic acid anhydride or an active ester thereof such as the N-hydroxysuccinimide ester is employed for the acylation process (not in accordance with the second aspect invention), the selective acylation of 3″-amino group cannot be achieved but there is involved by-formation of 1-N-acylated product and/or formation of mixed acylation products mainly comprising the 1-N-acylated product. It is worthy of attention that the aimed selective acylation of 3″-amino group cannot be then achieved when using an acid anhydride or active ester of the same alkanoic acid for the acylating agent.

The acylating agents of the formula (VIII) available in the second aspect invention are different in reactivity and their reactivity are in a wide range of from "strong" to "weak". When an acylating agent of a strong reactivity is employed, the acylating reaction may be conducted for a short reaction time under cooling. While, when an acylating agent of a weak reactivity is employed, the acylating reaction may be effected either under heating or for a prolonged reaction time. In general, however, the reaction temperature may suitably be in a range of $-30°$ to $+120°$ C. and the reaction time may appropriately be in a range of 30 minutes to 24 hours or even to 48 hours.

The desired selectively 3″-N-acylated product so obtained may be recovered from the reaction mixture in a known manner, for example, by evaporation of the solvent or by precipitation with addition of water, if necessary, followed by further purification of the product.

The reaction mechanism by which the selective 3″-N-acylation can be achieved according to the process of the second aspect of the invention is not yet fully elucidated. A possible interpretation is that the acylating agent of the formula (VIII) acylates at first a hydroxyl group of the starting material to form an ester product intermediately and this O-esterifying acyl group is then shifted or migrated to an amino group (corresponding the 3″-amino or 3″-alkylamino group in the case of the present process) when this amino group is neighboring to the esterified hydroxyl intermediately formed, whereby the acylation of said amino group is resulted in. If this assumption is followed, it is possible to explain the reason why the 1-amino group which has no neighboring hydroxyl group cannot be acetylated in the process of the second aspect invention. Besides, there is a fact that the intermediate ester product cannot be obtained when the trifluoroacetylation or formylation is conducted according to the process of the second aspect invention. Reason why the ester product cannot be recovered upon the trifluoroacetylation or formylation, is probably that the O-trifluoroacetyl group or O-formyl group is instable and that an amount of the instable O-acyl group which has not undergone the shifting to the amino group (namely, the known O→N acyl-migration) is removed from the acylated hydroxyl group in the course of recovery and purification of the 3″-N-acylation product so as to restore the free hydroxyl group. However, this invention is not limited to the above interpretation of the reaction mechanism involved in the present process. Anyhow, it seems that amongst the compounds which are available as the acylating agent of the formula (VIII) according to the second aspect of this invention, such ones are more suitable for the purpose of the second aspect invention if they have an acyl group which is likely to give a more instable ester product when this acyl group is transformed into an O-acyl group by reacting with hydroxyl group and thus giving the ester product. Meanwhile, it is very interesting to notice that when the process of the second aspect invention is carried out using in stead of the N-formylimidazol and N-alkanoyl-imidazole such as N-acetyl-imidazole, N-propionyl-imidazole and N-butyroyl-imidazole, the 3″-amino or 3″-alkylamino group of the partially protected N-acylated aminoglycosidic antibiotic derivative is not acylated but a hydroxyl group neighboring to said 3″-amino or 3″-alkylamino group can be esterified by the alkanoyl group of the N-alkanoyl-imidazole employed to give an intermediate O-esterification product. When this O-esterification product or the whole reaction mixture containing this O-esterification product is subsequently treated with an alkaline reagent such as ammonium hydroxide at ambient temperature, the O-esterifying alkanoyl group is caused to shift or migrate to the neighboring 3″-amino or 3″-alkylamino group, resulting in a selective acylation and hence protection of the 3″-amino or 3″-alkylamino group. Thus, the reaction mixture from the reaction of the partially protected N-acylated aminoglycosidic antibiotic derivative with an N-alkanoyl-imidazole is, at first, not found to contain the desired 3″-N-acylated product, but from said reaction mixture can be recovered the desired 3″-N-acylated product only after the reaction mixture has been made alkaline by treating with an alkaline reagent such as aqueous ammonia (see Example 71 given hereinafter).

As a valuable application of the processes of the first and second aspects of this invention, it is possible to provide a high-yield process for the production of the 1-N-acylated aminoglycosidic antibiotic which is known semi-synthetic antibacterial agent. Thus, this invention further includes a process of producing a 1-N-(α-hydroxy-ω-aminoalkyanoyl) aminoglycosidic antibiotic starting from the parent aminoglycosidic antibiotic, the process comprising a combination of the step of preparing by the aforesaid "zinc-complexing" process of the first aspect invention such a partially protected N-acylated aminoglycosidic antibiotic derivative in which 1-amino and 3"-amino or 3"-alkylamino groups are unprotected and all the other amino groups are protected; the step of preparing the 1-N-unprotected and other N-fully-protected derivative by the selective 3"-N-acylating process of the second aspect invention, the step of acylating 1-amino group of the 1-N-unprotected and other N-fully protected derivative obtained from the preceding 3"-N-acylation step, with an α-hydroxy-ω-aminoalkanoic acid, especially 3-amino-2-hydroxypropionic acid (isoserine) or 4-amino-2-hydroxybutyric acid; and finally the step of deprotecting from the 1-N-acylation product so obtained.

More particularly, according to the third aspect of this invention, there is provided an improved process of producing a 1-N-(α-hydroxy-ω-aminoalkanoyl) derivative of an aminoglycosidic antibiotic comprising a 6-0-(3"-amino- or 3"-alkylamino-3"-deoxyglycosyl)-2-deoxystreptamine moiety having optionally a 4-0-(aminoglycosyl) group, the process comprising the consecutive steps of:

(a) reacting zinc cations with the aminoglycosidic antibiotic in an inert organic solvent to produce the complex of zinc cations with the aminoglycosidic antibiotic, (b) reacting an acylation reagent having an acy group to be introduced as the amino-protecting group, with the aminoglycosidic antibiotic-zinc cation complex formed in the above step (a) in situ in the inert organic solvent, to produce a complex of zinc cations with the selectively N-acylated derivative of the aminoglycosidic antibiotic having the initially non-complexed amino groups acylated, (c) reacting the selectively N-acylated aminoglycosidic antibiotic derivative-zinc cation complex obtained in the above step (b), with a reagent which removes zinc cations from the N-acylated zinc complex, to give a partially and selectively protected N-acylated aminoglycosidic antibiotic derivative which is free from zinc cations and in which 1-amino and 3"-amino or 3"-alkylamino group are unprotected but all the other amino groups in the aminoglycoside molecule are protected by the acyl group, (d) reacting the partially and selectively protected N-acylated derivative obtained in the above step (c) with an alkanoic acid ester of the formula (VIII):

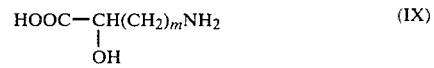

wherein $R^a$ is a hydrogen atom or a dihaloalkyl or trihaloalkyl group of 1–6 carbon atoms and $R^b$ is an alkyloxy group of 1–6 carbon atoms, an aralkyloxy group of 1–6 carbon atoms, particularly benzyloxy group or an aryloxy group, particularly phenoxy group, or N-formylimidazole as the acylating agent in an inert organic solvent to selectively acylate the 3"-amino or 3"-alkylamino group with the acyl group $R^aCO—$ of said acylating agent and thereby to give the 1-N-unprotected and other N-fully-acylated-protected derivative of the aminoglycosidic antibiotic in which all the amino groups other than 1-amino group are protected with acyl group, (e) reacting the 1-N-unprotected and other N-fully-protected derivative obtained in the preceding step (d) with an α-hydroxy-ω-aminoalkanoic acid of the formula (IX):

wherein m is 1 or 2 or an equivalent reactive derivative thereof of which the amino group is either unprotected or protected, to acylate 1-amino group of said 1-N-unprotected derivative, (f) and then removing the residual amino-protecting groups from the 1-N-acylation product obtained in the above step (e) by a conventional deprotecting method.

We describe below more fully how to carry out the process of the third aspect of this invention.

The aminoglycosidic antibiotics which are available as the initial material in the first step (a) of the present process are the same as those described hereinbefore in respect of the process of the first aspect of this invention, and the reaction of complexing zinc cations with the aminoglycosidic antibiotic is achieved in the same manner as described hereinbefore, too. The acylation of the aminoglycosidic antibiotic-zinc cation complex so obtained in the first step (a) may be effected in the second step (b) of the present process in the same way as described hereinbefore in respect of the process of the first aspect invention. The removal of zinc cations from the selectively N-acylated aminoglycosidic antibiotic-zinc cation complex so obtained may be conducted in the third step (c) of the present process in various ways as described before, whereby there is obtained a partially and selectively protected N-acylated aminoglycosidic antibiotic derivative which is free from zinc cations and in which 1-amino and 3"-amino or 3"-alkylamino groups are unprotected but all the other amino groups in the aminoglycoside molecule are blocked with the acyl group of the acylation reagent employed in the step (b) of the present process. This partially and selectively protected N-acylated derivative of the aminoglycosidic antibiotic is then reacted with an alkanoic acid ester of the formula (VIII) or N-formylimidazole in the step (d) of the present process in the same manner as described hereinbefore in respect of the process of the second aspect of this invention, to obtain the selective 3"-N-acylation of the partially N-protected aminoglycosidic antibiotic derivative without acylation of 1-amino group thereof.

In the fifth step (e) of the present process, the 1-N-unprotected and other N-fully-protected derivative of the aminoglycosidic antibiotic obtained in the preceding step (d) is reacted with an α-hydroxy-ω-aminoalkanoic acid of the formula (X), particularly 3-amino-2-hydroxypropionic acid (as DL-isoserine, D-isoserine or L-isoserine) or L-4-amino-2-hydroxybutyric acid to acylate 1-amino group of the aminoglycosidic antibiotic with the 3-amino-2-hydroxypropionyl or 4-amino-2-hydroxyburyryl group. This 1-N-acylation may be conducted generally as described in the specification of U.K. Pat. No. 1,426,908 or U.S. Pat. No. 4,001,208 according to any known method of synthesis of amides by reacting the protected aminoglycosidic antibiotic derivative with an isoserine or L-4-amino-2-hydroxybutyric acid, either in its free acid form or in the form of its reactive equivalent such as an active ester, eg. the dicyclohexylcarbodiimide ester, mixed acid anhydride, acid azide in an inert organic solvent such as dioxane, dimethoxyethane, dimethylformamide, tetrahydrofuran or aqueous ones of these solvents. Isoserine and L-4-amino-2-hydroxybutyric acid may be such ones of which amino group has been blocked with an amino-protecting group. Suitable amino-protecting group for this purpose may be the same as or different from that one which was used in the 1-N-unprotected but other N-fully-protected aminoglycosidic antibiotic derivative to be 1-N-acylated. t-Butoxycarbonyl group is a preferred amino-protecting group, as it is readily removable by treating with a dilute acid such as aqueous trifluoroacetic acid, aqueous acetic acid and diluted hydrochloric acid. Benzyloxycarbonyl group which is removed by conventional catalytic hydrogenolysis over palladium or platinum oxide catalyst, as well as phthaloyl group which is easily removed by hydrolysis with hydrazine are very convenient as the amino-protecting group to this end.

The acylating reaction in the 1-N-acylation step (e) of the process of the fourth aspect invention may preferably be conducted in an aqueous organic solvent using an active ester of the α-hydroxy-ω-aminoalkanoic acid (X). The suitable active ester may be N-hydroxysuccinimide ester of isoserine or L-4-benzyloxycarbonylamino-2-hydroxybutyric acid, and this active ester may be employed in a quantity of 1 to 2 mol., favorably of 1 to 1.5 mol. per mol. of the aminoglycoside to be 1-N-acylated. The water-miscible organic solvent for use in the reaction medium may preferably be dioxane, dimethoxyethane, dimethylformamide, tetrahydrofuran.

Subsequently to the above step (e), the N-deprotection step (f) of the present process is carried out to remove all the residual amino-protecting groups from the 1-N-acylation product obtained in the above step (e). The removal of the residual amino-protecting group may be achieved by a conventional N-deprotecting technique. Such a residual amino-protecting group which is of an alkoxycarbonyl type may be removed by hydrolysis with an aqueous solution of trifluoroacetic acid or acetic acid or with a diluted acid solution such as dilute hydrochloric acid. Such a residual amino-protecting group which is of an aralkyloxycarbonyl type, for example, benzyloxycarbonyl is readily removed by conventional catalytic hydrogenolysis. When all the residual amino-protecting groups are removed from the 1-N-acylation product of the step (e) of the present process, the desired 1-N-(2-hydroxy-3-aminopropionyl)- or 1-N-(2-hydroxy-4-aminobutyryl)-aminoglycosidic antibiotic is obtained in a high yield.

Examples of the 1-N-(α-hydroxy-ω-aminoalkanoyl)-aminoglycosidic antibiotic which is produced by the process of the fourth aspect invention are listed below.

(1) 1-N-(L-4-amino-2-hydroxybutyryl)-kanamycin A
(2) 1-N-(L-4-amino-2-hydroxybutyryl)-3'-deoxykanamycin A
(3) 1-N-(L-4-amino-2-hydroxybutyryl)-3',4'-dideoxykanamycin A
(4) 1-N-(L-4-amino-2-hydroxybutyryl)-tobramycin
(5) 1-N-(L-4-amino-2-hydroxybutyryl)-dibekacin
(6) 1-N-(3-amino-2-hydroxypropionyl)-dibekacin.

Another application of the processes of the first and second aspects of this invention is to produce 1-N-alkyl aminoglycosidic antibiotic from the all N-acylated aminoglycosidic derivatives containing unprotected 1-amino group, and an example of this application is to produce netilmicin or its 1-N-alkylanalogues from sisomicin by alkylation with a lower aliphatic aldehyde and cyanoborohydride.

This invention is further illustrated but not limited by the following Examples.

EXAMPLE 1

Preparation of 3,6'-di-N-benzyloxycarbonylkanamycin A (i) 2.0 g (4.13 m moles) of kanamycin A (free base) was suspended in a mixture of dimethylsulfoxide (50 ml) and tetrahydrofuran (20 ml) and 4 g (18.1 m moles) of zinc (II) acetate dihydrate was added to the suspension, followed by agitation at room temperature until the reaction mixture formed a homogeneous solution. It took about 4-5 hours for a zinc complex of kanamycin A to be formed and dissolve. The resultant solution was then cooled to 0° C., to which was slowly added over about one hour a cooled solution (at 0° C.) of 2.37 g (9.5 m moles) of N-benzyloxycarbonyloxysuccinimide

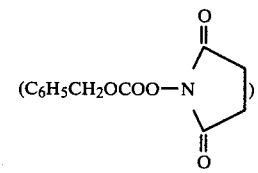

dissolved in a mixture (40 ml) of tetrahydrofuran-dimethylsulfoxide (1:1 by volume). The reaction solution was allowed to stand at ambient temperature for 4 hours, during which the zinc complex of kanamycin A had undergone benzyloxycarbonylation (the acylation according to the first aspect invention).

A sample taken from the reaction solution thus obtained was subjected to silica gel thin layer chromatography using as developing solvent the lower liquid phase of a mixture of chloroform-methanol-28% aqueous ammonia (1:1:1 by volume), which gave a main spot of the desired product at $R_f=0.23$ and two or three minor spots attributted to by-products at upper points.

(ii) The above reaction solution was poured into 500 ml of ethyl ether and the oil separated was washed several times with further volumes of ethyl ether to afford 8.8 g of a thick syrupy material.

(iii) Removal of zinc cation from the syrupy material (substantially comprising the zinc complex) was performed by either of the following different procedures:

(A) Procedure using a weakly acidic cation-exchange resin carrying carboxyl group (—COOH) as functional group (commercially available as "Amberlite" CG 50 resin (H+ form) from Rohm & Haas Co., U.S.A.)

60 ml of Amberlite CG 50 resin (H+ form) was preliminarily saturated thoroughly with a mixture of water-dioxane (2:1) and then packed in a column. A solution of 1 g of the syrupy substance dissolved in 20 ml of water-dioxane (1:1) was passed through the column, which was then developed with water-dioxane (2:1) containing 1% acetic acid. The eluate was collected in fractions. The desired 3,6'-di-N-benzyloxycarbonylkanamycin A which was positive to ninhydrin reaction was first eluted out of the column, and zinc acetate which was sensitive to coloration by diphenylcarbazide was then eluted out. The fractions containing the desired product were combined together and concentrated to dryness. The residue was washed with ethyl ether to give 340 mg (81%) of 3,6′-di-N-benzyloxycarbonylkanamycin A as colorless solid. $[\alpha]_D^{25} +76°$ (c 1, water-dimethylformamide, 1:2).

Elemental analysis: Calcd. for $C_{34}H_{48}N_4O_{15} \cdot 2CH_3CO_2H \cdot H_2O$: C, 51.23; H, 6.56; N, 6.29%. Found: C, 51.02; H, 6.71; N, 6.22%.

(B) Procedure using a weak cation-exchange resin bearing carboxylate group as functional group (commercially available as "Amberlite" CG 50 resin ($NH_4^+$ form) from Rohm & Haas Co.)

1 g of the syrup-like material obtained in the above Example 1 (ii) was dissolved in 20 ml of water-dioxane (1:1) and the solution was passed through a column of 60 ml of Amberlite CG 50 resin ($NH_4^+$ form) and subjected to linear gradient elution with water-dioxane (1:1) containing 0 to 0.1 N ammonia. No zinc cation was eluted but the desired product, 3,6′-di-N-benzyloxycarbonylkanamycin A was eluted. The fractions of the eluate containing the desired benzyloxycarbonylation product was concentrated to dryness to give 328 mg (89%) of the desired product as colorless solid. $[\alpha]_D^{25} = +86°$ (c 1, water-dimethylformamide, 1:2).

Elemental Analysis: Calcd. for $C_{34}H_{48}N_4O_{15} \cdot \frac{1}{2}H_2CO_3$: C, 52.87; H, 6.30; N, 7.15%. Found: C, 52.50; H, 6.59; N, 7.00%.

(C) Procedure using a cation-exchange resin bearing strongly acidic functional group —$SO_3H$ (commercially available as "Dowex" 50W×2 resin from Dow Chemical Co.)

30 ml of Dowex 50W×2 resin ($H^+$ form) which had been immersed in water-dioxane (2:1) was packed in a column, through which was then passed a solution of 1 g of the syrup-like material obtained in Example 1 (ii) in 20 ml of water-dioxane (2:1). The column was washed with water-dioxane (2:1) until the effluent from the column showed neutral nature, and then linear gradient elution was made with water-dioxane (2:1) containing 0 to 1 N ammonia. The eluate fractions containing the desired 3,6′-di-N-benzyloxycarbonylkanamycin A was concentrated to dryness under reduced pressure to afford 311 mg (84%) of a white solid which was identical to that obtained in Example 1 (iii) (B).

(D) Alternative procedure using Dowex 50W×2

A solution of 1 g of the syrup-like material obtained in Example 1 (ii) in 20 ml of water-methanol (3:1) was charged into a column of 30 ml of Dowex 50W×2 ($H^+$ form) previously wetted with water-methanol (3:1). The column was well washed with water-methanol (3:1), then gradient elution was made with water-methanol (3:1) containing 0 to 6 N hydrochloric acid. The active fractions containing the desired 3,6′-di-N-benzyloxycarbonylkanamycin A were collected and admixed with a strongly basic anion-exchange resin, Dowex 1×2 resin (OH form) in an amount sufficient to make the admixture slightly acidic.

The admixture was filtered and the filtrate was concentrated to dryness to give 285 mg (72%) of the desired product in the form of dihydrochloride. $[\alpha]_D^{25} +79°$ (c 1, water-dimethylformamide, 1:2).

(E) Procedure using an anion-exchange resin carrying strongly basic functional quaternary ammonium group (commercially available as Dowex 1×2 resin from Dow Chemical Co.)

A solution of 1 g of the syrup-like material obtained in Example 1 (ii) in water-dioxane (1:1) was placed in a column of 30 ml of Dowex 1×2 resin (OH form) previously impregnated with water-dioxane (1:1), and then the column was developed with water-dioxane (1:1) at a relatively high speed. The eluate fractions containing the desired product were collected and concentrated to dryness to give 305 mg (84%) of a colorless solid which was identical to that of Example 1 (iii) (B).

(F) Procedure using an anion-exchange resin bearing weakly basic functional group (commercially available as Dowex WGR resin, a product of Dow Chemical Co.)

1 g of the syrup-like material obtained in Example 1 (ii) was dissolved in 20 ml of water-dioxane (2:1) and the solution was passed through a column of 50 ml of Dowex WGR resin (base form) previously saturated with water-dioxane (2:1), followed by elution with water-dioxane (2:1). The desired 3,6′-di-N-benzyloxycarbonylkanamycin A was eluted out in some fractions together with a trace of zinc cation entrained. These fractions were combined together and concentrated to dryness to afford 450 mg of a colorless solid. The solid could be directly used as starting material for the production of 1-N-((S)-4-amino-2-hydroxybutyryl) kanamycin A according to the 1-N-acylation method of Example 31 given hereinafter, wherein the trace of zinc cation remaining in the solid starting material has no adverse influence on the acylation reaction involved in Example 31.

(G) Procedure using a chelate-exchange resin carrying weakly acidic functional group (commercially available as Dowex A 1 resin, a product of Dow Chemical Co., U.S.A.)

A solution of 1 g of the syrupy material obtained in Example 1 (ii) in water-dioxane (1:1) was introduced into a column of 50 ml of Dowex A 1 resin which had been saturated with water-dioxane (1:1) containing 1% ammonia, followed by gradient elution with mixtures of water-dioxane (1:1) containing 0 to 1 N ammonia. The eluate fractions containing the desired 3,6′-di-N-benzyloxycarbonylkanamycin A which were eluted only in a later phase as the effluent from the column, were combined together and concentrated to dryness to give 272 mg (74%) of the desired product as a white solid.

(H) Procedure using Chitosan (a water-insoluble polymer containing functional groups capable of combining with a metal, commercially available as a product of Toko Kasei Koyo Co., Ltd., Japan)

100 ml of Chitosan was thoroughly impregnated with water-methanol (3:1) and packed in a column, through which was then passed a solution of 1 g of the syrupy material obtained in Example 1 (ii) in water-methanol (3:1). The column was subjected to development with water-methanol (3:1), when the desired 3,6′-di-N-benzyloxycarbonylkanamycin A was first eluted and zinc acetate was eluted much later. The eluate fractions containing the former were combined and concentrated to dryness to leave a residue, which was dissolved in water-dioxane (1:1) and the solution was placed in a column of Amberlite CG 50 resin ($NH_4^+$ form) pretreated with water-dioxane (1:1). The column was well washed with water-dioxane (1:1) and then subjected to gradient elution with water-dioxane (1:1) containing 0 to 0.1 N ammonia. Those fractions sensitive to ninhydrin reaction were combined together and concentrated to dryness to give 301 mg (82%) of a colorless solid which was identical to that obtained in Example 1 (iii) (B).

(I) A procedure using a high polymer bearing carboxyl functional groups (commercially available as "CM-Sephadex" C-25, which is an ion-exchange gel-filtration agent consisting of a carboxymethyl-substituted dextran gel, a product of Pharmacia Fine Chemical Co., Sweden)

A solution of 1 g of the syrupy material obtained in Example 1 (ii) in water-dioxane (1:1) was passed through a column of 40 ml of CM-Sephadex C-25 ($NH_4^+$ form) which had been well saturated with water-dioxane (1:1). The column was washed with 200 ml of water-dioxane (1:1) and then subjected to gradient elution using water-dioxane (1:1) containing 0 to 0.1 N ammonia. No zinc cation was eluted out of the column but only the desired 3,6'-di-N-benzyloxycarbonylkanamycin A eluted. The eluate was concentrated to dryness to give 303 mg (82%) of a colorless solid identical to that of Example 1 (iii) (B).

(J) A procedure using hydrogen sulfide as zinc-precipitating agent 1 g of the syrupy material obtained in Example 1 (ii) was dissolved in 20 ml of water-methanol (1:1), to which was then added aqueous ammonia, followed by introduction of a sufficient amount of hydrogen sulfide. The reaction mixture containing the zinc sulfide precipitate formed was filtered on a glass filter which was filled with "Celite" filter aid, and the filtrate was concentrated under reduced pressure to leave a syrupy material, which was well washed with ethyl ether to give a solid residue. This residue was taken up in a volume of water-dioxane (1:1) and the solution was chromatographed on a column of 30 ml of Amberlite IRA 900 (OH form, strongly basic resin, a product of Rohm & Haas Co.) using water-dioxane (1:1) as developing solvent. The eluate was collected in fractions, and the fractions containing 3,6'-di-N-benzyloxycarbonylkanamycin A were combined together and concentrated to dryness to give 235 mg (64%) of a colorless solid which was identical to that of Example 1 (iii) (B).

EXAMPLE 2

Preparation of 3,6'-di-N-benzyloxycarbonylkanamycin A 500 mg (1.03 m moles) of kanamycin A (free base) was suspended in 15 ml of dimethylsulfoxide, to which were then added 420 mg (3.09 m moles) of zinc chloride and 840 mg (6.18 m moles) of sodium acetate trihydrate. After stirring the mixture at ambient temperature for 10 hours, to the mixture containing the kanamycin A-zinc complex formed was slowly added over about one hour a solution of 675 mg (2.27 m moles) of N-benzyloxycarbonyloxyphthalimide

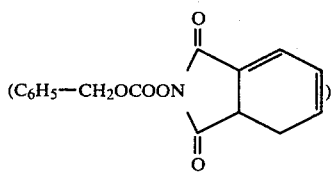

dissolved in 10 ml of dimethylsulfoxide. The resultant mixture was allowed to stand at room temperature for 4 hours.

Subsequently, the reaction mixture was treated in the same manner as described in Example 1 (ii) and (iii) (I) to yield 598 mg (74%) of 3,6'-di-N-benzyloxycarbonylkanamycin A in the form of colorless solid.

EXAMPLE 3

Preparation of 3,6'-di-N-benzyloxycarbonylkanamycin A 600 mg (0.95 m moles) of kanamycin A tetrahydrochloride and 150 mg (3.8 m moles) of sodium hydroxide in 15 ml of dimethylsulfoxide were agitated for one hour, to which was then added 1 g (4.55 m moles) of zinc acetate dihydrate, followed by continued agitation for further 5 hours. To the mixture containing the kanamycin A-zinc complex formed was added over 30 minutes a solution of 545 mg (2.2 m moles) of N-benzyloxycarbonyloxysuccinimide dissolved in 5 ml of dimethylsulfoxide-tetrahydrofuran (1:1). After agitating the resultant mixture at ambient temperature overnight, ethyl ether was added thereto to deposit the N-acylated zinc complex as a precipitate. The precipitate was then treated following the same procedure as described in Example 1 (iii) (H) to give 581 mg (78%) of a colorless solid of the titled compound.

EXAMPLE 4

Preparation of 3,6'-di-N-benzyloxycarbonylkanamycin A (i) 500 mg (1.03 m moles) of kanamycin A (free base) was dissolved in 20 ml of a mixture of water-dimethylsulfoxide (1:9), to which were then added 1 g (4.55 m moles) of zinc acetate dihydrate and subsequently 590 mg (2.4 m moles) of N-benzyloxycarbonyloxysuccinimide. After allowing the mixture to stand at ambient temperature overnight, a great amount of ethyl ether was added to the mixture, resulting in separation of a watery syrup layer, which was washed several times with ethyl ether to give a thick syrupy layer.

(ii) The syrupy material thus obtained was dissolved in water-methanol (3:1) and the solution was passed through a column of 200 ml of Chitosan. The column was eluted with water-methanol (3:1) and the eluate was collected in fractions. The fractions positive to ninhydrin reaction were combined together and concentrated to a small volume. The concentrate was placed into a column of Amberlite CG 50 resin ($NH_4^+$ form) and the column was well washed with a mixture of water-dioxane (1:1) and then subjected to gradient elution with water-dioxane (1:1) containing 0 to 0.1 N ammonia. The eluate fractions containing the desired product were combined together and concentrated to dryness to afford 494 mg (61%) of a colorless solid which was identical to that obtained in Example 1 (iii) (B).

EXAMPLE 5

Preparation of 3,6'-di-N-benzyloxycarbonylkanamycin A 500 mg (1.03 m moles) of kanamycin A (free base) was dissolved in 20 ml of a mixture of water-tetrahydrofuran (1:3), to which was then added 1 g (4.55 m moles) of zinc acetate dihydrate, followed by addition of 590 mg (2.4 m moles) of N-benzyloxycarbonyloxysuccinimide. The mixture was allowed to stand at ambient temperature overnight and the reaction solution so obtained was concentrated under reduced pressure. The residue was passed through a column of 200 ml of Chitosan and the effluent coming from the column was subsequently treated in the same way as in Example 4 (ii) to give 414 mg (51%) of a colorless solid of the titled compound.

EXAMPLE 6

Preparation of 3,6'-di-N-benzyloxycarbonylkanamycin A (i) 500 mg (1.03 m moles) of kanamycin A (free base) was dissolved in 15 ml of a mixture of water-methanol (1:7), to which was then added 1.5 g (6.8 m moles) of zinc acetate dihydrate, followed by addition of 590 mg (2.4 m moles) of N-benzyloxycarbonyloxysuccinimide in 7 ml of tetrahydrofuran. The mixture was allowed to stand at ambient temperature overnight and the reaction solution so obtained was concentrated under reduced pressure. The residue was passed through a column of 200 ml of Chitosan and the effluent coming out of the column was subsequently treated in the same way as in Example 4 (ii) to give 442 mg (55%) of a colorless solid of the titled compound.

EXAMPLE 7

Preparation of 3,6'-di-N-benzyloxycarbonylkanamycin A 500 mg (1.03 m moles) of kanamycin A (free base) was suspended in 20 ml of dimethylsulfoxide and 272 mg (1.24 m moles) of zinc acetate dihydrate was added to the suspension. The mixture was stirred at room temperature for 10 hours to form a substantially transparent solution, to which was then added in small portions over about two hours 540 mg (2.17 m moles) of N-benzyloxycarbonyloxysuccinimide. After allowing the resultant mixture to stand at ambient temperature overnight, a large volume of ethyl ether was added and the oily material separated was taken off and washed several times with ethyl ether to give a thick syrupy material.

Silica gel thin layer chromatography of a sample taken from the syrupy material using chloroform-methanol-28% aqueous ammonia (1:1:1 by volume, lower phase) as developing solvent indicated the following spots:
- minor spot at $R_f$ 0.4 of 1,3,6',3''-tetra-N-benzyloxycarbonylkanamycin A (which developed a color by being sprayed with sulfuric acid and then heating);
- faint spot at $R_f$ 0.28;
- main spot at $R_f$ 0.23 of the desired product, 3,6'-di-N-benzyloxycarbonylkanamycin A;
- minor spot at $R_f$ 0.12 of 6'-N-benzyloxycarbonylkanamycin A; and
- extremely weak spot at $R_f$ 0 of unreacted kanamycin A.

No spot corresponding to tri-N-benzyloxycarbonylkanamycin A was substantially observed which might appear at $R_f$ 0.28 to 0.4.

The above thick syrupy material was dissolved in water-dioxane (1:1) and the solution was passed through a column of 100 ml of CM-Sephadex C-25 resin ($NH_4^+$ form) previously wetted with water-dioxane (1:1). Subsequently, the column was subjected to the elution process in the same way as described in Example 1 (iii) (I), whereby zinc cation was removed and the desired product separated from the other products to yield 412 mg (51%) of the titled compound as colorless solid.

By way of comparison, the procedure as mentioned just above was repeated but replacing the zinc acetate dihydrate by 308 mg (1.24 m moles) of nickel (II) acetate tetrahydrate, with the result that the desired 3,6'-di-N-benzyloxycarbonylkanamycin A was obtained as colorless solid only in a poor yield of 59 mg (7.3%).

EXAMPLE 8

Preparation of 3,6'-di-N-(p-methoxybenzyloxycarbonyl) kanamycin A 500 mg (1.03 m moles) of kanamycin A (free base) was suspended in 12 ml of dimethylsulfoxide and 1 g (4.55 m moles) of zinc acetate dihydrate was added to the suspension. The mixture was stirred at room temperature until it formed a homogeneous solution, to which was then added over approx. 30 minutes a solution of 789 mg (2.6 m moles) of p-methoxycarbobenzoxy p-nitrophenyl ester (p-$CH_3OC_6H_4CH_2OCOOC_6H_4$p-$NO_2$) dissolved in 10 ml of dimethylsulfoxide. The resultant mixture was allowed to stand overnight at ambient temperature and subsequently treated in the same manner as in Example 1 (ii) and (iii) (B) to afford 722 mg (83%) of a colorless solid of the titled compound. $[\alpha]_D^{25} + 87°$ (c 1, water-dimethylformamide, 1:2).

Elemental Analysis: Calcd. for $C_{36}H_{52}N_4O_{17}.\frac{1}{2}H_2CO_3$: C, 51.95; H, 6.33; N, 6.64%. Found: C, 51.56; H, 6.41; N, 6.53%.

EXAMPLE 9

Preparation of 6'-N-(t-butoxycarbonyl) kanamycin A

Following the same procedure as described in Example 8 except that the p-methoxycarbobenzoxy p-nitrophenyl ester was replaced by 220 mg (1.54 m moles) of t-butoxycarbonylazide, the titled compound was obtained in the form of colorless solid. Yield 627 mg. $[\alpha]_D^{25} = +96°$ (c 1, water-dimethylformamide, 1:2).

EXAMPLE 10

Preparation of 3,6'-di-n-trifluoroacetylkanamycin A 500 mg (1.03 m moles) of kanamycin A (free base) was suspended in 12 ml of dimethylsulfoxide and 1 g (4.55 m moles) of zinc acetate dihydrate was added to the suspension. The mixture was stirred at room temperature until it formed a homogeneous solution, to which was then added a solution of 1.2 g (5.1 m moles) of p-nitrophenol ester of trifluoroacetic acid dissolved in 10 ml of dimethylsulfoxide. The resultant mixture was allowed to stand overnight at ambient temperature and subsequently treated with ethyl ether as set out in Example 1 (ii). The ether-insoluble syrupy material was further treated in the same way as in Example 1 (iii) (A) to give 590 mg (70%) of the titled compound in the form of colorless solid. $[\alpha]_D^{25} + 81°$ (c 1, water-dimethylformamide, 1:2).

Elemental Analysis: Calcd. for $C_{22}H_{34}N_4O_{13}F_6.2CH_3CO_2H.H_2O$: C, 38.33; H, 5.44; N, 6.88; F, 13.99%. Found: C, 38.03; H, 5.48; N, 6.54%.

EXAMPLE 11

Preparation of 3,6'-di-N-phenoxycarbonylkanamycin A 500 mg (1.03 m moles) of kanamycin A (free base) was suspended in a mixture of dimethylsulfoxide (15 ml) and tetrahydrofuran (5 ml) and 1 g (4.55 m moles) of zinc acetate dihydrate was added to the suspension, followed by agitation at room temperature until the reaction mixture formed a homogeneous solution. The resultant solution was then cooled to 0° C., to which was slowly added a cooled solution (at 0° C.) of 400 mg (2.55 m moles) of phenoxycarbonyl chloride ($C_6H_5OCOCl$) in 3 ml of tetrahydrofuran. The reaction solution was brought to room temperature over one hour and then allowed to stand at that temperature for 3 hours. Subsequently, the reaction mixture was treated with ethyl ether as mentioned in Example 1 (ii) and the ether-insoluble syrupy material was further treated by the same procedure as in Example 1 (iii) (A) to give 625 mg (70%) of a colorless solid of the titled compound. $[\alpha]_D^{25} + 73°$ (c 1, water-dimethylformamide, 1:2).

Elemental Analysis: Calcd. for $C_{32}H_{44}N_4O_{15} \cdot 2CH_3CO_2H \cdot H_2O$: C, 50.11; H, 6.31; N, 6.49%. Found: C, 49.77; H, 6.60; N, 6.11%.

EXAMPLE 12

Preparation of 3,6'-di-N-acetylkanamycin A

The reaction mixture obtained by the same procedure as in Example 8 except using 260 mg (2.6 m moles) of acetic anhydride in place of the p-methoxycarbobenzoxy p-nitrophenyl ester was treated in the same way as described in Example 1 (iii) (A). There was thus prepared 525 mg (72%) of the titled compound as colorless solid. $[\alpha]_D^{25} = +93°$ (c 1, water-dimethylformamide, 1:2).

Analysis: Calcd. for $C_{22}H_{40}N_4O_{13} \cdot 2CH_3CO_2H \cdot H_2O$: C, 44.19; H, 7.13; N, 7.93%. Found: C, 44.20; H, 7.07; N, 7.85%.

EXAMPLE 13

Preparation of 3,6'-di-N-formylkanamycin A 500 mg (1.03 m moles) of kanamycin A (free base) was suspended in 12 ml of dimethylsulfoxide and 1 g (4.55 m moles) of zinc acetate dihydrate was added to the suspension. The mixture was stirred at room temperature until it formed a homogeneous solution, to which was then added 690 mg (4.12 m moles) of p-nitrophenylformate ($OHCOC_6H_4$-p-$NO_2$). The resultant mixture was allowed to stand overnight at ambient temperature and subsequently treated in the same manner as in Example 1 (iii) (H). The fractions positive to ninhydrin reaction were combined together, bubbled with gaseous carbon dioxide and then concentrated to dryness. There was thus obtained 430 mg (67%) of the titled compound as colorless solid. $[\alpha]_D^{25} + 101°$ (c 1, water).

Analysis: Calcd. for $C_{20}H_{36}N_4O_{13} \cdot H_2CO_3 \cdot H_2O$: C, 40.64; H, 6.50; N, 9.03%. Found: C, 40.43; H, 6.47; N, 8.83%.

EXAMPLE 14

Preparation of 3,6'-di-N-tosylkanamycin A 500 mg (1.03 m moles) of kanamycin A (free base) was suspended in 15 ml of dimethylsulfoxide and 1 g (4.55 m moles) of zinc acetate dihydrate was added to the suspension. The mixture was stirred at room temperature until it formed a homogeneous solution, to which was then added slowly a solution of 400 mg (2.1 m moles) of tosyl chloride in 7 ml of tetrahydrofuran. The resultant mixture was allowed to stand at ambient temperature for one hour, followed by further addition of 200 mg of tosyl chloride dissolved in 3.5 ml of tetrahydrofuran. The reaction mixture was allowed to stand for further two hours and then treated by the procedure identical to that described in Example 1 (ii) and (iii) (A), affording 270 mg (28%) of a colorless solid of the titled compound. $[\alpha]_D^{25} + 68°$ (c 1, water-dimethylformamide, 1:2).

Analysis: Calcd. for $C_{32}H_{48}N_4O_{15}S_2 \cdot 2CH_3CO_2H \cdot H_2O$: C, 46.44; H, 6.28; N, 6.02; S, 6.89%. Found: C, 46.31; H, 5.98; N, 6.31; S, 6.55%.

Where the above reaction procedure was repeated but omitting zinc acetate, no substantial amount of the colorless solid was recovered.

EXAMPLE 15

Preparation of 3,6'-di-N-benzyloxycarbonyl-6'-N-methylkanamycin A 500 mg (1.0 m mole) of 6'-N-methyl-kanamycin A (free base) was suspended in 12 ml of dimethylsulfoxide and 1 g (4.55 m moles) of zinc acetate dihydrate was added to the suspension. The mixture was stirred at room temperature until it formed a homogeneous solution, to which was then added over 30 minutes a solution of 550 mg (2.2 m moles) of N-benzyloxycarbonyloxysuccinimide dissolved in 5 ml of dimethylsulfoxide-tetrahydrofuran (1:1). The resultant mixture was allowed to stand overnight at ambient temperature and subsequently treated in the same manner as in Example 1 (ii) and (iii) (A) to afford 720 mg (79%) of a colorless solid of the title compound. $[\alpha]_D^{25} + 74°$ (c 1, water-dimethylformamide, 1:2).

The subsequent treatment of the titled compound by the procedure similar to that described in Example 31 hereinbelow gave 1-N-((S)-4-amino-2-hydroxybutyryl)-6'-N-methylkanamycin A.

EXAMPLE 16

Preparation of 3,6'-di-N-benzyloxycarbonyl-3'-deoxykanamycin A

The titled compound in the form of colorless solid was obtained in a yield of 765 mg (82%) by repeating the same procedure as in Example 15 but starting from 500 mg (1.07 m moles) of 3'-deoxykanamycin A (free base) and using 610 mg (2.45 m moles) of N-benzyloxycarbonyloxysuccinimide. $[\alpha]_D^{25} = +76°$ (c 1, water-dimethylformamide, 1:2).

Analysis: Calcd. for $C_{34}H_{48}N_4O_{14} \cdot 2CH_3CO_2H \cdot H_2O$: C, 52.16; H, 6.68; N, 6.40%. Found: C, 51.99; H, 6.75; N, 6.20%.

The subsequent treatment of the titled compound by the procedure similar to that described in Example 31 gave 1-N-((S)-4-amino-2-hydroxybutyryl)-3'-deoxykanamycin A.

EXAMPLE 17

Preparation of 3,6'-di-N-benzyloxycarbonyl-3'-deoxy-6'-N-methylkanamycin A

The titled compound was obtained in a yield of 737 mg (80%) by repeating the same procedure as in Example 15 but starting from 500 mg (1.04 m moles) of 3'-deoxy-6'-N-methylkanamycin A (free base) and using 595 mg (2.4 m moles) of N-benzyloxycarbonyloxysuccinimide. $[\alpha]_D^{25} + 73°$ (c 1, water-dimethylformamide, 1:2).

The subsequent treatment of the titled compound by the procedure similar to that described in Example 31 gave 1-N-((S)-4-amino-2-hydroxybutyryl)-3'-deoxy-6'-N-methylkanamycin A.

EXAMPLE 18

Preparation of
3,6'-di-N-benzyloxycarbonyl-4'-deoxykanamycin A

Starting from 500 mg (1.07 m moles) of 4'-deoxykanamycin A free base (see "Journal of Antibiotics", Vol. 27, pp. 838–849 (1974); "Bulletin of the Chemical Society of Japan", Vol. 50, pp. 2362–2368 (1977)), the titled compound in the form of colorless solid was obtained in a yield of 666 mg (71%) by the same procedure as in Example 15 except that 580 mg (2.3 m moles) of N-benzyloxycarbonyloxysuccinimide dissolved in 4 ml of dimethylsulfoxide was slowly added over one hour to the homogeneous solution. $[\alpha]_D^{25} = +77°$ (c 1, water-dimethylformamide, 1:2).

Analysis: Calcd. for $C_{34}H_{48}N_4O_{18}.2CH_3CO_2H.H_2O$: C, 52.16; H, 6.68; N, 6.40%. Found: C, 51.77; H, 6.79; N, 6.31%.

EXAMPLE 19

Preparation of
3,2',6'-tri-N-benzyloxycarbonylkanamycin B 500 mg (1.03 m moles) of kanamycin B (free base) was suspended in a mixture of 12 ml of dimethylsulfoxide and 4 ml of tetrahydrofuran and 1 g (4.55 m moles) of zinc acetate dihydrate was added to the suspension. The mixture was stirred at room temperature until it formed a homogeneous solution, and then cooled to 0° C. Into the cooled solution was slowly added over one hour a cold solution of 825 mg (3.3 m moles) of N-benzyloxycarbonyloxysuccinimide dissolved in 10 ml of tetrahydrofuran-dimethylsulfoxide (1:1). The resultant mixture was allowed to stand at 0° C. for 2 hours and then at ambient temperature overnight, whereupon the mixture was treated in the same way as stated in Example 1 (ii) and (iii) (A) to yield 740 mg (70%) of the titled compound as colorless solid. $[\alpha]_D^{25} = +63°$ (c 1, water-dimethylformamide, 1:2).

Analysis: Calcd. for $C_{42}H_{55}N_5O_{16}.2CH_3CO_2H.H_2O$: C, 53.95; H, 6.40; N, 6.84%. Found: C, 53.66; H, 6.67; N, 6.63%.

The subsequent treatment of the titled compound by the procedure similar to that described in Example 31 gave 1-N-((S)-4-amino-2-hydroxybutyryl) kanamycin B.

EXAMPLE 20

Preparation of
3,2',6'-tri-N-benzyloxycarbonyltobramycin 480 mg (1.03 m moles) of tobramycin (free base) was suspended in 12 ml of dimethylsulfoxide and 1 g (4.55 m moles) of zinc acetate dihydrate was added to the suspension. The mixture was stirred at room temperature during one hour to form a homogeneous solution, to which was then added over approx. one hour a solution of 850 mg (3.4 m moles) of N-benzyloxycarbonyloxysuccinimide dissolved in 10 ml of tetrahydrofuran-dimethylsulfoxide (1:1). After allowing the mixture to stand at ambient temperature overnight, the reaction solution obtained was treated with a large volume of ethyl ether as mentioned in Example 1 (ii) to give a thick syrupy material.

The syrupy material was further treated in the same way as in Example 1 (iii) (A) but using water-dioxane (1:2 instead of 2:1) to afford 810 mg (78%) of the titled compound as a colorless solid. $[\alpha]_D^{25} = +65°$ (c 1, water-dimethylformamide, 1:2).

Analysis: Calcd. for $C_{42}H_{55}N_5O_{15}.2CH_3CO_2H.H_2O$: C, 54.81; H, 6.50; N, 6.95%. Found: C, 54.77; H, 6.71; N, 6.88%.

The subsequent treatment of the titled compound by the procedure similar to that described in Example 31 gave 1-N-((S)-4-amino-2-hydroxybutyryl)-tobramycin.

EXAMPLE 21

Preparation of
3,2',6'-tri-N-benzyloxycarbonyl-6'-N-methyltobramycin

The titled compound in the form of colorless solid was obtained in a yield of 890 mg (84%) by repeating the same procedure as in Example 20 but starting from 500 mg (1.04 m moles) of 6'-N-methyltobramycin (free base). $[\alpha]_D^{25} = +63°$ (c 1, water-dimethylformamide, 1:2).

EXAMPLE 22

Preparation of
3,2',6'-tri-N-benzyloxycarbonyl-4'-deoxykanamycin B

Starting from 480 mg (1.03 m moles) of 4'-deoxykanamycin B free base (see "Bulletin of the Chemical Society of Japan", Vol. 50, pp. 2362–2368 (1977)), the titled compound in the form of colorless solid was obtained in a yield of 815 mg (79%) by the same procedure as in Example 20. $[\alpha]_D^{25} + 63°$ (c 1, water-dimethylformamide, 1:2).

EXAMPLE 23

Preparation of
3,2',6'-tri-N-benzyloxycarbonyldibekacin 600 mg (1.33 m moles) of dibekacin (3',4'-dideoxykanamycin B) (free base) was suspended in 15 ml of dimethylsulfoxide and the suspension was agitated to form a solution, to which was added 1.4 g (6.4 m moles) of zinc acetate dihydrate, followed by further agitation. To the resultant solution was slowly added over about one hour a solution of 1.1 g (4.4 m moles) of N-benzyloxycarbonyloxysuccinimide in 12 ml of dimethylsulfoxide, and the mixture was allowed to stand at ambient temperature overnight. Then, a large volume of ethyl ether was admixed with the reaction solution to separate an oily deposit (mainly comprising the N-benzyloxycarbonylated dibekacin-zinc complex as the desired product and a proportion of dimethylsulfoxide), which was washed with ethyl ether to give a thick syrupy material.

This syrupy material was repeatedly washed with water, whereby the N-acylated zinc complex was destroyed with water and the liberated zinc cation removed together with the initially existing excess of zinc acetate. There was thus obtained 1.1 g of a water-insoluble solid comprising the N-acylated dibekacin. The solid was subjected to silica gel thin layer chromatography using chloroform-ethanol-18% aqueous ammonia (1:1:1, lower phase) as developing solvent to give a single spot at $R_f$ 0.3, indicating that the solid consisted essentially of 3,2',6'-tri-N-benzyloxycarbonyldibekacin with a trace of zinc.

The subsequent treatment of the titled compound by the procedure similar to that described in Example 31 gave 1-N-((S)-4-amino-2-hydroxybutyryl)-dibekacin.

For further purification, the crude product as obtained above of the titled compound was washed with 3 M ammonia solution to give product without contamination of zinc ion. $[\alpha]_D^{25} +71°$ (c 1, water-dimethylformamide, 1:2).

EXAMPLE 24

Preparation of 3,2',6'-tri-N-benzyloxycarbonyl-6'-N-methyldibekacin 500 mg (1.07 m moles) of 6'-N-methyldibekacin (free base) and 1.2 g (5.45 m moles) of zinc acetate dihydrate were dissolved in 20 ml of dimethylsulfoxide, to which was slowly added over about 30 minutes 910 mg (3.6 m moles) of N-benzyloxycarbonyloxysuccinimide. The reaction solution was allowed to stand at ambient temperature overnight and subsequently treated in the same way as mentioned in Example 23, affording 910 mg of the titled compound which was substantially pure.

The subsequent treatment of the titled compound by the procedure similar to that described in Example 31 gave 1-N-((S)-4-amino-2-hydroxybutyryl)-6'-N-methyldibekacin.

EXAMPLE 25

Preparation of 3,2'-di-N-benzyloxycarbonylkanamycin C

The titled compound in the form of colored solid was obtained in a yield of 730 mg (79%) by following the same procedures as described in Example 1 (i), (ii) and (iii) A but starting from 500 mg (1.03 m moles) of kanamycin C (free base). $[\alpha]_D^{25} +75°$ (c 1, water-dimethylformamide, 1:2).

The subsequent treatment of the titled compound by the procedure similar to that described in Example 31 gave 1-N-((S)-4-amino-2-hydroxybutyryl)-kanamycin C.

EXAMPLE 26

Preparation of 6'-N-benzyloxycarbonylkanamycin A 500 mg (1.03 m moles) of kanamycin A (free base) was suspended in 20 ml of dimethylsulfoxide and 0.5 g (2.3 m moles) of zinc acetate dihydrate was added to the suspension. The mixture was stirred at room temperature until it formed a homogeneous solution, to which was then added 283 mg (1.13 m moles) of N-benzyloxycarbonyloxysuccinimide. The resultant mixture was allowed to stand overnight at ambient temperature and subsequently treated in the same manner as in Example 1 (ii) and (iii) (I) to afford 556 mg of the titled compound as a colorless solid. $[\alpha]_D^{25} = +92°$ (c 1, water).

EXAMPLE 27

Preparation of 6'-N-benzyloxycarbonyldibekacin

Following the procedure as described in Example 26, 382 mg of the titled compound was obtained using 500 mg of dibekacin (free base), 12 ml of dimethylsulfoxide, 0.7 g of zinc acetate dihydrate and 305 mg of N-benzyloxycarbonyloxysuccinimide. $[\alpha]_D^{25} +105°$ (c 0.5, water).

EXAMPLE 28

Preparation of 3,2',6'-tri-N-benzyloxycarbonyl-3',4'-dideoxy-3'-enokanamycin B 500 mg (1.11 m moles) of 3',4'-dideoxy-3'-enokanamycin B free base (see "Bulletin of the Chemical Society of Japan", Vol. 50, pp. 1580-1583 (1977)) was dissolved in 12 ml of dimethylsulfoxide, and 1 g (4.55 m moles) of zinc acetate dihydrate was added to the solution, followed by agitation for one hour. To the resultant solution was slowly added over 30 minutes 870 mg (3.49 m moles) of N-benzyloxycarbonyloxysuccinimide. After allowing the mixture to stand at ambient temperature overnight, the reaction solution obtained was treated with a large volume of ethyl ether as mentioned in Example 1 (ii) to give a thick syrupy material.

The syrupy material was further treated in the same way as in Example 1 (iii) (B) but using water-dioxane (1:2 instead of 2:1) to afford 784 mg of the titled compound as colorless solid. $[\alpha]_D^{25} +30°$ (c 1, water-dimethylformamide, 1:2).

EXAMPLE 29

Preparation of 3,2',6'-tri-N-benzyloxycarbonylsisomicin

The titled compound in the form of colorless solid was obtained in a yield of 780 mg by following the same procedure as in Example 28 but starting from 500 mg (1.12 m moles) of sisomicin (free base). $[\alpha]_D^{25} = +110°$ (c 1, water-dimethylformamide, 1:2).

EXAMPLE 30

Preparation of 3,2',6'-tri-N-benzyloxycarbonylgentamicins 787 mg of the titled compound was obtained in the form of colorless solid by following the same procedure as in Example 28 but starting from 500 mg of mixed gentamicins (C, $C_{1a}$, $C_2$ etc.).

EXAMPLE 31 (as a reference)

Preparation of 1-N-((S)-4-amino-2-hydroxybutyryl) kanamycin A(amikacin)

55 mg (0.062 m moles) of 3,6'-di-N-benzyloxycarbonyl kanamycin A acetate prepared as described in Example 1 was dissolved in 1.5 ml of water-tetrahydrofuran (2:5), to which were added 13 mg (0.12 m moles) of anhydrous sodium carbonate and subsequently 23 mg (0.066 m moles) of N-hydroxysuccinimide ester of (S)-4-benzyloxycarbonylamino-2-hydroxybutyric acid. The mixture was allowed to stand at ambient temperature for 10 hours. The reaction solution obtained was concentrated to a small volume and the concentrate was taken up in 4 ml of water-dioxane (1:1). A small amount of acetic acid was added to the solution to render it weakly acidic, and the solution was subjected to hydrogenolysis by passing therethrough hydrogen gas under atmospheric pressure for one hour in the presence of palladium black (for removal of benzyloxycarbonyl group). The resultant reaction solution was filtered and concentrated and the concentrate was passed through a column of CM-Sephadex C-25 ($NH_4^+$ form) (a product of Pharmacia Fine Chemical Co., Sweden). The column was subjected to gradient elution with 0 to 0.5 N aqueous ammonia. The eluate fractions containing the desired product were combined together and concentrated to dryness to give 24 mg (yield 60%) of the titled compound as its monocarbonate, whose physical properties and antibacterial potency were identical to those of an authentic sample.

EXAMPLE 32 (as a reference)

Preparation of 1-N-(DL-isoseryl)dibekacin 58 mg (0.06 m moles) of 3,2',6'-tri-N-benzyloxycarbonyl dibekacin prepared as in Example 23 was dissolved in 1.5 ml of water-tetrahydrofuran (2:5), to which were added 13 mg (0.12 m moles) of anhydrous sodium carbonate and then 21 mg (0.063 m moles) of N-hydroxysuccinimide ester of N-benzyloxycarbonyl-DL-isoserine. The mixture was allowed to stand at room temperature and subsequently treated by the procedure as described in Example 31 to afford 21 mg (yield 59%) of the titled compound as its monocarbonate, whose physical properties and antibacterial potency were identical to those of an authentic sample.

EXAMPLE 33

Production of 3,6'-di-N-benzyloxycarbonyl-3''-N-trifluoroacetylkanamycin A

A solution of 504 mg of 3,6'-di-N-benzyloxycarbonylkanamycin A (see Example 1) in 4 ml of dimethylsulfoxide was admixed with 220 mg of ethyl trifluoroacetate, and the admixture obtained was allowed to stand overnight at ambient temperature. After a small amount of trifluoroacetic acid was added to the reaction mixture, the reaction solution was poured into a large volume of ethyl ether and the resultant oily material deposited was washed well with ethyl ether to afford the solidified material. This material was dried well to obtain 640 mg of the titled compound as a solid substance. Yield 99%, $[\alpha]_D^{25} + 98°$ (c 1, pyridine)

Elemental analysis: Calcd. for $C_{36}H_{47}N_4O_{16}F_3 \cdot CF_3COOH$ C 47.40; H 5.02; N 5.82%. Found: C 47.13; H 5.15; N 5.79%.

EXAMPLE 34

Production of 3,6'-di-N-benzyloxycarbonyl-3''-N-trifluoroacetylkanamycin A

A solution of 20 mg of 3,6'-di-N-benzyloxycarbonylkanamycin A in 0.4 ml of dimethylsulfoxide was admixed with 6 mg of phenyl trifluoroacetate, and the admixture obtained was allowed to stand overnight at ambient temperature. Subsequently, the reaction mixture was processed in the same manner as in Example 33, affording 24.8 mg of the titled product which was found identical to that of Example 33. Yield 97%.

EXAMPLE 35

Production of 3,6'-di-N-benzyloxycarbonyl-3''-N-trifluoroacetylkanamycin A

A solution of 10 mg of 3,6'-di-N-benzyloxycarbonylkanamycin A in 0.3 ml of hexamethylphosphoric triamide was admixed with 7 mg of ethyl trifluoroacetate, and the admixture obtained was allowed to stand overnight at ambient temperature. The reaction solution was admixed with a small volume of trifluoroacetic acid and then poured into a large volume of ethyl ether. The oily material deposited was washed well with ethyl ether and the resultant solid substance dried to give 11.7 mg (yield 91%) of the titled product as its mono-trifluoroacetate in the form of a solid.

EXAMPLE 36

Production of 3,6'-di-N-benzyloxycarbonyl-3''-N-trifluoroacetylkanamycin A

A suspension of 10 mg of 3,6'-di-N-benzyloxycarbonylkanamycin A in 0.3 ml of dimethylformamide was admixed with 7 mg of ethyl trifluoroacetate, and the admixture obtained was allowed to stand overnight at ambient temperature. The homogeneous reaction solution thus obtained was admixed with a small volume of trifluoroacetic acid and then poured into a large volume of ethyl ether. The oily material deposited was washed well with ethyl ether to solidify it and the resultant solid substance dried, affording 11.5 mg (Yield 90%) of the titled product as its monotrifluoroacetate in the form of a solid.

EXAMPLE 37

Production of 3,6'-di-N-benzyloxycarbonyl-3''-N-trifluoroacetylkanamycin A

A suspension of 10 mg of 3,6'-di-N-benzyloxycarbonylkanamycin A in 0.35 ml of sulfolane was admixed with 7 mg of ethyl trifluoroacetate, and the admixture was stirred overnight at ambient temperature. Subsequently, the reaction mixture was processed in the same manner as in Example 33, affording 12.0 mg (Yield 94%) of the titled product as the mono-trifluoroacetate in the form of a solid substance.

EXAMPLE 38

Production of 3,6'-di-N-benzyloxycarbonyl-3''-N-trifluoroacetylkanamycin A

A suspension of 22 mg of 3,6'-di-N-benzyloxycarbonylkanamycin A in 0.8 ml of tetrahydrofuran was admixed with 10 mg of ethyl trifluoroacetate, and the admixture was stirred for 2 days. The resulting homogeneous reaction solution was admixed with 15 mg of ethyl trifluoroacetate and 8 mg of anhydrous sodium carbonate, stirred overnight and then allowed to stand for 2 days. The resultant reaction solution was concentrated to a small volume, and the concentrate was washed with water and then dried to give a solid material. The solid material was suspended in a small volume of tetrahydrofuran together with a small amount of trifluoroacetic acid. The admixture so obtained was stirred followed by addition of ethyl ether. The precipitated solid was filtered off, washed with ether and dried, giving 21 mg (Yield 74%) of the titled product mono-trifluoroacetate as a solid substance. $[\alpha]_D^{25} + 98°$ (c 1, Pyridine).

EXAMPLE 39

Production of 3,6'-di-N-benzyloxycarbonyl-3''-N-trifluoroacetylkanamycin A

A solution of 10 mg of 3,6'-di-N-benzyloxycarbonylkanamycin A in water-tetrahydrofuran (1:1, 0.3 ml) was admixed with a solution of 5 mg of ethyl trifluoroacetate in 0.1 ml tetrahydrofuran, and the resultant admixture was allowed to stand at ambient temperature for one day. Subsequently, a mixture of ethyl trifluoroacetate (10 mg), anhydrous sodium carbonate (4.4 mg) and tetrahydrofuran (0.1 ml) was added to the resultant solution at 5 hours intervals (four times in all) to effect the 3″-N-trifluoroacetylation. The reaction solution was concentrated and then treated in the same manner as in Example 38 to give 5.5 mg (Yield 43%) of the titled product mono-trifluoroacetate as a solid substance.

EXAMPLE 40

Production of 3,6′-di-N-benzyloxycarbonyl-3″-N-trifluoroacetylkanamycin A

A solution of 10 mg of 3,6′-di-N-benzyloxycarbonylkanamycin A in water-ethanol (2:3, 0.6 ml) was admixed with a soluion of 5 mg of ethyl trifluoroacetate in 0.1 ml of tetrahydrofuran, and the admixture was allowed to stand at ambient temperature for one day. The reaction solution was thereafter processed in the same way as in Example 38, affording 2.3 mg (Yield 18%) of the titled product monotrifluoroacetate as a solid substance.

EXAMPLE 41

Production of 3,6′-di-N-t-butoxycarbonyl-3″-N-trifluoroacetylkanamycin A (a) Preparation of 3,6′-di-N-t-butoxycarbonylkanamycin A 500 mg (1.03 m moles) of kanamycin A (free base) was suspended in 12 ml of dimethylsulfoxide, and 1 g (4.55 m moles) of zinc acetate dihydrate was added to the suspension obtained. The mixture was stirred at room temperature until it formed a homogenous solution, to which was then added 370 mg (2.59 m moles) of t-butoxycarbonyl azide. The resultant mixture was allowed to stand overnight at room temperature and subsequently treated in the same manner as described in Example 1 (ii) and (iii) B to afford 590 mg (80%) of a colorless solid of the titled compound. $[\alpha]_D^{25} + 89°$ (c 1, water-dimethylformamide, 1:2)

(b) Production of 3,6′-di-N-t-butoxycarbonyl-3″-N-trifluoroacetylkanamycin A 3,6′-di-N-t-butoxycarbonylkanamycin A (60 mg) was dissolved in 0.5 ml of dimethylsulfoxide, and the resulting solution was admixed with 25 mg of ethyl trifluoroacetate, followed by allowing the admixture obtained to stand overnight at ambient temperature. Subsequently, the reaction solution was processed in the same manner as described in Example 33, giving 76.8 mg (Yield 98%) of the titled compound trifluoroacetate as a solid. $[\alpha]_D^{25} + 72°$ (c 1, water-dimethylformamide, 1:2).

Elemental analysis: Calcd. for $C_{30}H_{51}N_4O_{16}F_3 \cdot CF_3COOH$: C 42.95; H 5.86; N 6.26%. Found: C 42.77; H 5.92; N 6.38%.

EXAMPLE 42

Production of 3,6′-di-N-(p-methoxybenzyloxycarbonyl)-3″-N-trifluoroacetylkanamycin A A solution of 40 mg of 3,6′-di-N-(p-methoxybenzyloxycarbonyl)kanamycin A (see Example 8 hereinbefore) in 0.4 ml of dimethylsulfoxide was admixed with 18 mg of ethyl trifluoroacetate, and the admixture was allowed to stand overnight at ambient temperature. Subsequently, the reaction solution was processed in the same manner as in Example 33, affording 49.3 mg (Yield 98%) of the titled compound as a solid substance. $[\alpha]_D^{25} + 78°$ (c 1, water-dimethylformamide, 1:2).

Elemental analysis: Calcd. for $C_{38}H_{51}N_4O_{18}F_3 \cdot CF_3COOH$: C 46.97; H 5.12; N 5.48%. Found: C 47.18; H 5.03; N 5.31%.

EXAMPLE 43

Production of 3,6′,3″-tri-N-trifluoroacetylkanamycin A 75 mg of 3,6′-di-N-trifluoroacetylkanamycin A (see Example 10 hereinbefore) and triethylamine (12 mg) were admixed with 0.6 ml of dimethylsulfoxide and then with 35 mg of ethyl trifluoroacetate, and the admixture was stirred overnight to effect the desired 3″-N-trifluoroacetylation. The reaction solution was then processed in the same manner as in Example 33, affording 94.2 mg (Yield 96%) of the titled compound as a solid substance. $[\alpha]_D^{25} + 76°$ (c 1, water-dimethylformamide, 1:2).

Elemental analysis: Calcd. for $C_{24}H_{33}N_4O_{14}F_9 \cdot CF_3COOH$ C 35.22; H 3.87; N 6.32%. Found: C 35.09; H 3.99; N 6.07%.

EXAMPLE 44

Production of 3,6′-di-N-phenoxycarbonyl-3″-N-trifluoroacetylkanamycin A

A solution of 53 mg of 3,6′-di-N-phenoxycarbonylkanamycin A (see Example 11) and triethylamine (9 mg) in 0.5 ml of dimethylsulfoxide was admixed with 23 mg of methyl trifluoroacetate, and the admixture was then processed in the same manner as in Example 33, affording 65 mg (Yield 95%) of the titled compound as a solid material. $[\alpha]_D^{25} + 70°$ (c 1, water-dimethylformamide, 1:2).

Elemental analysis: Calcd. for $C_{34}H_{43}N_4O_{16}F_3 \cdot CF_3COOH$ C 46.26; H 4.74; N 5.99%. Found: C 45.88; H 4.96; N 5.77%.

EXAMPLE 45

Production of 3,6′,3″-tri-N-formylkanamycin A

A mixture of 62 mg of 3,6′-di-N-formylkanamycin A (see Example 13), 90 mg of ethyl formate and 1 ml of dimethylsulfoxide was heated at 100° C. for 12 hours in a sealed tube to effect the desired 3″-N-formylation. The reaction solution was admixed with a little amount of formic acid, then poured into a large volume of ethyl ether, and processed in the same manner as in Example 33, affording 69 mg (Yield 98%) of the title compound as a solid material positive to ninhydrin. $[\alpha]_D^{25} + 109°$ (c 1, water-dimethylformamide, 1:2).

Elemental analysis: Calcd. for $C_{21}H_{36}N_4O_{14} \cdot HCOOH$ C 43.00; H 6.23; N 9.12%. Found: C 42.83; H 6.19; N 9.10%.

EXAMPLE 46

Production of 3,6′-di-N-benzyloxycarbonyl-6′-N-methyl-3″-N-trifluoroacetylkanamycin A A mixture of 68 mg of 3,6′-di-N-benzyloxycarbonyl-6′-N-methylkanamycin A (see Example 15), and triethylamine (11 mg), 30 mg of ethyl trifluoroacetate and 0.7 ml of dimethylsulfoxide was treated in the same manner as in Example 33, affording 86 mg (Yield 99%) of the titled compound mono-trifluoroacetate as a solid substance. $[\alpha]_D^{25} + 65°$ (c 1, water-dimethylformamide, 1:2).

EXAMPLE 47

Production of 3,6'-di-N-benzyloxycarbonyl-3'-deoxy-3''-N-trifluoroacetylkanamycin A A solution of 52 mg of 3,6'-di-N-benzyloxycarbonyl-3'-deoxykanamycin A (see Example 16) and triethylamine (11 mg) in 0.4 ml of dimethylsulfoxide was admixed with 21 mg of ethyl trifluoroacetate, and the admixture was allowed to stand overnight at ambient temperature. Subsequently, the reaction solution was processed in the same manner as in Example 33, affording 64.8 mg (Yield 97%) of the titled compound as a solid material. $[\alpha]_D^{25} +70°$ (c 1, water-dimethylformamide, 1:2).

Elemental analysis: Calcd. for $C_{36}H_{47}N_4O_{15}F_3 \cdot CF_3COOH$ C 48.21; H 5.11; N 5.92%. Found: C 47.94; H 5.35; N 5.77%.

EXAMPLE 48

Production of 3,6'-di-N-benzyloxycarbonyl-3'-deoxy-3''-N-formylkanamycin A

A solution of 78 mg of 3,6'-di-N-benzyloxycarbonyl-3'deoxykanamycin A in 0.7 ml of dimethylsulfoxide was admixed with 65 mg of phenyl formate, and the admixture was heated overnight at 50° C. for the 3''-N-formylation. The reaction solution was admixed with a small amount of formic acid, and processed in the same manner as in Example 33, giving 83 mg (Yield 97%) of the titled compound monoformate as a solid substance. $[\alpha]_D^{25} +84°$ (c 1, water-dimethylformamide, 1:2).

EXAMPLE 49

Production of 3,6'-di-N-benzyloxycarbonyl-3''-N-dichloroacetyl-3''-deoxykanamycin A A solution of 35 mg of 3,6'-di-N-benzyloxycarbonyl-3'-deoxykanamycin A in 0.5 ml of dimethylsulfoxide was admixed with 12 mg of methyl dichloroacetate, and the admixture was allowed to stand overnight at ambient temperature. The reaction solution was admixed with a small volume of dichloroacetic acid and then treated in the same manner as in Example 33, giving 44.5 mg (Yield 96%) of the titled compound as a solid substance. $[\alpha]_D^{25} +65°$ (c 1, water-dimethylformamide, 1:2).

Elemental analysis: Calcd. for $C_{36}H_{48}N_4O_{15}Cl_2 \cdot CHCl_2COOH$ C 46.73; H 5.16; N 5.74; Cl 14.52%. Found: C 46.58; H 5.33; N 5.62; Cl 14.28%.

EXAMPLE 50

Production of 3,6'-di-N-benzyloxycarbonyl-3''-N-trichloroacetyl-3'-deoxykanamycin A A solution of 58 mg of 3,6'-di-N-benzyloxycarbonyl-3'-deoxykanamycin A in 0.7 ml of dimethylsulfoxide was admixed with 25 mg of methyl trichloroacetate, and the admixture was allowed to stand overnight at 50° C. The reaction solution was admixed with a small volume of trichloroacetic acid and then processed in the same manner as in Example 33, affording 80.5 mg (Yield 98%) of the titled compound as a solid substance. $[\alpha]_D^{25} +65°$ (c 1, water-dimethylformamide, 1:2).

Elemental analysis: Calcd. for $C_{36}H_{47}N_4O_{15}Cl_3 \cdot CCl_3CO_2H$ C 43.65; H 4.63; N 5.36; Cl 20.34%. Found: C 43.44; H 4.77; N 5.30; Cl 20.19%.

EXAMPLE 51

Production of 3,6'-di-N-benzyloxycarbonyl-3'-deoxy-3''-N-trifluoroacetyl-6''-N-methylkanamycin A A solution of 72 mg of 3,6'-di-N-benzyloxycarbonyl-3'-deoxy-6''-N-methylkanamycin A in 1 ml of dimethylsulfoxide was admixed with 30 mg of ethyl trifluoroacetate, and the admixture was allowed to stand overnight at ambient temperature. Subsequently, the reaction solution was processed in the same manner as in Example 33, affording 89.5 mg (Yield 97%) of the titled compound, mono-trifluoroacetate as a solid substance. $[\alpha]_D^{25} +70°$ (c 1, water-dimethylformamide, 1:2).

EXAMPLE 52

Production of 3,6'-di-N-benzyloxycarbonyl-4'-deoxy-3''-N-trifluoroacetylkanamycin A A solution of 71 mg of 3,6'-di-N-benzyloxycarbonyl-4'-deoxykanamycin A (see Example 18 hereinbefore) triethylamine (12 mg) and 30 mg of ethyl trifluoroacetate in 1 ml of dimethylsulfoxide was processed in the same manner as in Example 33, giving 90 mg (Yield 99%) of the titled compound mono-trifluoroacetate as a solid substance. $[\alpha]_D^{25} +72°$ (c 1, water-dimethylformamide, 1:2).

EXAMPLE 53

Production of 3,6'-di-N-benzyloxycarbonyl-3',4'-dideoxy-3''-N-trifluoroacetylkanamycin A A solution of 75 mg of 3,6'-di-N-benzyloxycarbonyl-3',4'-dideoxykanamycin A and 30 mg of ethyl trifluoroacetate in 1 ml of dimethylsulfoxide was treated in the same manner as in Example 33, affording 96 mg (Yield 99%) of the titled compound as a solid substance. $[\alpha]_D^{25} +72°$ (c 1, water-dimethylsulfoxide, 1:2).

Elemental analysis: Calcd. for $C_{36}H_{47}N_4O_{14}F_3 \cdot CF_3COOH$: C 49.03; H 5.20; N 6.02%. Found: C 48.83; H 5.46; N 5.87%.

EXAMPLE 54

Production of 3,6'-di-N-benzyloxycarbonyl-3',4'-dideoxy-3''-N-formylkanamycin A 75 mg of 3,6'-di-N-benzyloxycarbonyl-3',4'-dideoxykanamycin A and 65 mg of phenyl formate were dissolved in 1 ml of dimethylsulfoxide and the resultant solution was processed in the same manner as in Example 48, affording 80 mg (Yield 97%) of the titled compound monoformate as a solid substance. $[\alpha]_D^{25} +80°$ (c 1, water-dimethylformamide, 1:2).

EXAMPLE 55

Production of 3,6'-di-N-benzyloxycarbonyl-3',4'-dideoxy-3''-N-dichloroacetylkanamycin A A solution of 68 mg of 3,6'-di-N-benzyloxycarbonyl-3',4'-dideoxykanamycin A in 0.9 ml of dimethylsulfoxide was admixed with 25 mg of methyl dichloroacetate, and the admixture was allowed to stand overnight at ambient temperature. The reaction solution was admixed with a small amount of dichloroacetic acid and then processed in the same manner as in Example 33, affording 88 mg (Yield 97%) of the titled compound mono-dichloroacetate as a solid substance. $[\alpha]_D^{25}+67°$ (c 1, water-dimethylformamide, 1:2).

EXAMPLE 56

Production of 3,2',6'-tri-N-benzyloxycarbonyl-3''-N-trifluoroacetylkanamycin B

A solution of 78 mg of 3,2',6'-tri-N-benzyloxycarbonylkanamycin B (see Example 19 hereinbefore) and triethylamine (11 mg) in 1 ml of dimethylsulfoxide was admixed with 35 mg of ethyl trifluoroacetate, and the admixture was processed in the same manner as in Example 33, affording 92 mg (Yield 95%) of the titled compound monotrifluoroacetate as a solid substance. $[\alpha]_D^{25}+60°$ (c 1, water-dimethylformamide, 1:2).

EXAMPLE 57

Production of 3,2',6'-tri-N-benzyloxycarbonyl-3''-N-formyltobramycin

A solution of 82 mg of 3,2',6'-tri-N-benzyloxycarbonyl-tobramycin (see Example 20 hereinbefore) and triethylamine (12 mg) in 1.2 ml of dimethylsulfoxide was admixed with 60 mg of phenyl formate, and the admixture was processed in the same manner as in Example 48, affording 86 mg (Yield 97%) of the titled compound as a solid substance. $[\alpha]_D^{25}+71°$ (c 1, water-dimethylformamide, 1:2).

Elemental analysis: Calcd. for $C_{43}H_{55}N_5O_{16}$.HCOOH C 55.98; H 6.09; N 7.42%. Found: C 55.50; H 6.22; N 7.28%.

EXAMPLE 58

Production of 3,2',6'-tri-N-benzyloxycarbonyl-6'-N-methyl-3''-N-trifluoroacetyltobramycin A solution of 80 mg of 3,2',6'-tri-N-benzyloxycarbonyl-6'-N-methyltobramycin (see Example 21 hereinbefore) and triethylamine (12 mg) in 1.2 ml of dimethylsulfoxide was admixed with 30 mg of ethyl trifluoroacetate, and the admixture was then processed in the same manner as in Example 33, affording 97 mg (Yield 98%) of the titled compound mono-trifluoroacetate as a solid substance. $[\alpha]_D^{25}+60°$ (c 1, water-dimethylformamide, 1:2).

EXAMPLE 59

Production of 3,2',6'-tri-N-benzyloxycarbonyl-3''-N-trifluoroacetyldibekacin

A solution of 82 mg of 3,2',6'-tri-N-benzyloxycarbonyl-dibekacin (see Example 23 hereinbefore) in 1 ml of dimethylsulfoxide was admixed with 30 mg of ethyl trifluoroacetae, and the admixture was processed in the same manner as in Example 33, affording 100 mg (Yield 98%) of the titled compound as a solid substance. $[\alpha]_D^{25}+61°$ (c 1, water-dimethylformamide, 1:2).

Elemental analysis: Calcd. for $C_{44}H_{54}N_5O_{15}F_3$.CF$_3$COOH C 51.93; H 5.21; N 6.58%. Found: C 51.84; H 5.38; N 6.47%.

EXAMPLE 60

Production of 3,2',6',3''-tetra-N-trifluoroacetyldibekacin

A mixture of 71 mg of 3,2',6'-tri-N-trifluoroacetyldibekacin and 30 mg of ethyl trifluoroacetate in 1 ml of dimethylsulfoxide was allowed to stand overnight at 40° C. Subsequently, the reaction solution was processed in the same manner as in Example 33, affording 90 mg (Yield 99%) of the titled compound as a solid substance. $[\alpha]_D^{25}+70°$ (c 1, water-dimethylformamide, 1:2).

Elemental analysis: Calcd. for $C_{26}H_{33}N_5O_{12}F_{12}$.CF$_3$COOH: C 35.42; H 3.61; N 7.38%. Found: C 35.40; H 3.89; N 7.17%.

EXAMPLE 61

Production of 3,2',6'-tri-N-benzyloxycarbonyl-3''-N-formyldibekacin

A mixture of 79 mg of 3,2',6'-tri-N-benzyloxycarbonyl-dibekacin and 60 mg of phenyl formate in 1.1 ml of dimethylsulfoxide was processed in the same manner as in Example 48, affording 84 mg (Yield 98%) of the titled compound monoformate as a solid substance. $[\alpha]_D^{25}+70°$ (c 1, water-dimethylformamide, 1:2).

EXAMPLE 62

Production of 3,2',6'-tri-N-benzyloxycarbonyl-3''-N-dichloroacetyldibekacin

A solution of 84 mg of 3,2',6'-tri-N-benzyloxycarbonyl-dibekacin in 1.2 ml of dimethylsulfoxide was reacted with 25 mg of methyl dichloroacetate in the same manner as in Example 49, affording 104 mg (Yield 97%) of the titled compound mono-dichloroacetate as a solid substance. $[\alpha]_D^{25}+59°$ (c 1, water-dimethylformamide, 1:2).

EXAMPLE 63

Production of 3,2',6'-tri-N-benzyloxycarbonyl-6'-N-methyl-3''-N-trifluoroacetyldibekacin A solution of 85 mg of 3,2',6'-tri-N-benzyloxycarbonyl-6'-N-methyldibekacin (see Example 24) in 1 ml of dimethylsulfoxide was admixed with 30 mg of ethyl trifluoroacetate, and the admixture was processed in the same manner as in Example 33, affording 103.5 mg (Yield 98%) of the titled compound mono-trifluoroacetate as a solid substance. $[\alpha]_D^{25}+60°$ (c 1, water-dimethylformamide, 1:2).

EXAMPLE 64

Production of 3,2'-di-N-benzyloxycarbonyl-3''-N-formylkanamycin C

A solution of 81 mg of 3,2'-di-N-benzyloxycarbonylkanamycin C (see Example 25) and triethylamine (14 mg) in 1.5 ml of dimethylsulfoxide was admixed with 90 mg of ethyl formate, and the admixture obtained was treated in the same manner as in Example 48, affording 85.5 mg (Yield 96%) of the titled compound monoformate as a solid substance. $[\alpha]_D^{25}+81°$ (c 1, water-dimethylformamide, 1:2).

EXAMPLE 65

Production of 3,2',6'-tri-N-benzyloxycarbonyl-3''-N-trifluoroacetylsisomicin

A solution of 82 mg of 3,2',6'-tri-N-benzyloxycarbonyl-sisomicin (see Example 29 hereinbefore) in 1.5 ml of dimethylsulfoxide was admixed with 30 mg of ethyl trifluoroacetate, and the admixture was processed in the same manner as in Example 33, affording 99 mg (Yield 97%) of the titled compound mono-trifluoroacetate as a solid substance. $[\alpha]_D^{25} +151°$ (c 1, water-dimethylformamide, 1:2).

EXAMPLE 66

Production of 3,2',6'-tri-N-benzyloxycarbonyl-3''-N-trifluoroacetyl-netilmicin

A solution of 85 mg of 3,2',6'-tri-N-benzyloxycarbonyl-netilmicin in 1.3 ml of dimethylsulfoxide was admixed with 30 mg of ethyl trifluoroacetate, and the admixture was processed in the same manner as in Example 33, affording 103 mg (Yield 98%) of the titled compound monotrifluoroacetate as a solid substance. $[\alpha]_D^{25} +145°$ (c 1, water-dimethylformamide, 1:2).

EXAMPLE 67

Production of 3,6'-di-N-benzyloxycarbonyl-3''-N-trifluoroacetylgentamicin B

A solution of 72 mg of 3,6'-di-N-benzyloxycarbonyl-gentamicin B in 1.2 ml of dimethylsulfoxide was admixed with 30 mg of ethyl trifluoroacetate, and the admixture was processed in the same manner as in Example 33, affording 91 mg (Yield 99%) of the titled compound mono-trifluoroacetate as a solid substance. $[\alpha]_D^{25} +92°$ (c 1, water-dimethylformamide, 1:2).

EXAMPLE 68

Production of 3,2',6'-tri-N-benzyloxycarbonyl-3''-N-trifluoroacetyl-gentamicin $C_1$ and $C_{1a}$ mixture A solution of 84 mg of 3,2',6'-tri-N-benzyloxycarbonyl-gentamicin $C_1$ and $C_{1a}$ mixture in 1.5 ml of dimethylsulfoxide was admixed with 30 mg of ethyl trifluoroacetate, and the resultant admixture was processed in the same manner as in Example 33, affording 101 mg of the titled compound mono-trifluoroacetate as a solid substance. $[\alpha]_D^{25} +87°$ (c 1, water-dimethylformamide, 1:2).

EXAMPLE 69

Production of 3,2',6'-tri-N-benzyloxycarbonyl-3',4'-dideoxy-3'-eno-3''-N-trifluoroacetylkanamycin B A mixture of 83 mg of 3,2',6'-tri-N-benzyloxycarbonyl-3',4'-dideoxy-3'-eno-kanamycin B (see Example 28 hereinbefore) and 35 mg of ethyl trifluoroacetate in 1.2 ml of dimethylsulfoxide was allowed to stand overnight at ambient temperature. Subsequently, the reaction solution was processed in the same manner as in Example 33, affording 99.5 mg (Yield 96%) of the titled compound mono-trifluoroacetate as a solid substance. $[\alpha]_D^{25} +26°$ (c 1, water-dimethylformamide, 1:2).

EXAMPLE 70

Production of 3,6'-di-N-benzyloxycarbonyl-3'-deoxy-3''-N-formylkanamycin A

A solution of 90 mg of 3,6'-di-N-benzyloxycarbonyl-3'-deoxykanamycin A in 0.8 ml of dimethylsulfoxide was admixed with 13 mg of N-formylimidazole, and the admixture was allowed to stand at ambient temperature overnight. The reaction solution was admixed with a little amount of formic acid and then treated with ethyl ether as in Example 33, affording 94 mg (Yield 95%) of the titled compound monoformate as a solid substance.

EXAMPLE 71

Production of 3,6',3''-tri-N-acetylkanamycin A

A mixture of 100 mg of 3,6'-di-N-acetylkanamycin A and 20 mg (1.03 molar proportion for 1 mol of the starting material) of N-acetylimidazole in 1 ml of dimethylsulfoxide was stirred under ice-cooling for 3 hours and then allowed to stand at ambient temperature overnight. The reaction solution was made alkaline by admixing with 0.3 ml of 28% aqueous ammonia and then allowed to stand at ambient temperature for 3 days. The resultant reaction mixture was treated with ethyl ether to give an ether-insoluble syrup. The syrup was taken up into water and then passed through a column of CM-Sephadex C-25 ($NH_4^+$-form) (a product of Pharmacia Fine Chemicals Co., Sweden). The resin column was developed with 0.05 N aqueous ammonia. The fractions containing the desired product eluted out were combined together and concentrated to dryness. The concentrate was taken up into water, and the aqueous solution was neutralized with acetic acid and again concentrated to dryness, affording 109 mg (Yield 90%) of the titled compound as a solid product. $[\alpha]_D^{25} +98°$ (c 1, water-dimethylformamide, 1:2).

Elemental analysis: Calcd. for $C_{24}H_{42}N_4O_{14}\cdot CH_3COOH\cdot H_2O$ C 45.34; H 7.02; N 8.14%. Found: C 45.22; H 7.20; N 8.11%.

EXAMPLE 72

Synthesis of 1-N-(L-4-amino-2-hydroxybutyryl)kanamycin A (amikacin)

(a) Preparation of 3,6'-di-N-benzyloxycarbonyl)kanamycin A (i) A suspension of 2.0 g (4.13 millimol) of kanamycin A (free base) in a mixed solvent of dimethylsulfoxide (50 ml) and tetrahydrofuran (20 ml) was admixed with 4 g (18.1 millimol) of zinc (II) acetate dihydrate, and the resulting admixture was stirred at ambient temperature until the reaction admixture formed a homogeneous solution. It took about 4–5 hours by the suspended kanamycin A dissolved with forming a kanamycin A-zinc cation complex. The resulting solution was then cooled to 0° C., and to this solution was dropwise added over about one hour a cold solution (at 0° C.) of 2.37 g (9.5 millimol) of N-benzyloxycarbonyloxysuccinimide in 40 ml of a mixed solvent of tetrahydrofuran-dimethylsulfoxide (1:1 by volume). Then the reaction solution was allowed to stand for 4 hours at ambient temperature. During the period of this time, the zinc complex of kanamycin A was subjected to benzyloxycarbonylation. The resulting reaction solution was subjected to silica gel thin-layer chromatography using a lower layer of chloroform-methanol-28% aqueous ammonia (1:1:1 by volume) as the development solvent, and it was then observed that the silica gel plate showed a main spot at Rf 0.23 and two or three slightly perceptible minor spots which are above the main spot and attributable to other by-products.

(ii) The reaction solution containing the N-benzyloxycarbonylated kanamycin A-zinc cation complex obtained in the above stage (i) was poured into 500 ml of ethyl ether, and the precipitated oily product was then washed with ethyl ether several times to give 8.8 g of a thick syrup-like product comprising the N-benzyloxycarbonylated complex.

(iii) Removal of the zinc cation from the syrupy complex product was made in the undermentioned way using a weakly acidic cation-exchange resin containing carboxylic functions (—COOH) [Amberlite CG-50 resin ($H^+$-form), a product of Rohm and Haas Co., U.S.A.].

60 ml of Amberlite CG-50 ($H^+$-form) resin was previously saturated well with water-dioxane (2:1 by volume). A column was filled with this resin, and then a solution of 1 g of the syrupy complex product in water-dioxane (1:1 by volume) was passed through the column, which was then developed with water-dioxane (2:1 by volume) containing 1% acetic acid. The eluate fractions containing the desired product, 3,6'-di-N-benzyloxycarbonyl-kanamycin A positive to ninhydrin firstly run out, and then the fractions containing zinc acetate positive to colorization with diphenylcarbazide were collected. The former fractions containing the desired product were combined together and concentrated to dryness, and the concentrate was washed with ethyl ether to give 340 mg (Yield 81%) of 3,6'-di-N-benzyloxycarbonyl-kanamycin A in the form of a colorless solid. $[\alpha]_D^{25} + 76°$ (c 1, water-dimethylformamide, 1:2)

Elemental analysis: Calcd. for $C_{34}H_{48}N_4O_{15} \cdot 2CH_3CO_2H—H_2O$ C51.23; H 6.56; N 6.29%. Found: C 51.02; H 6.71; N 6.22%.

(b) Preparation of
3,6'-di-N-benzyloxycarbonyl-3"-N-trifluoroacetylkanamycin A trifluoroacetate.

The product obtained in the above procedure (a) was process in the same way as in Example 33 but with addition of 1.5 molar equivalent of triethylamine, affording the titled compound.

(c) Preparation of
1-N-(L-4-amino-2-hydroxybutyryl)kanamycin A

A solution of 60 mg of 3,6'-di-N-benzyloxycarbonyl-3"-N-trifluoroacetylkanamycin A trifluoroacetate obtained in the above procedure (b) in 1.5 ml of water-tetrahydrofuran (1:1 by volume) was admixed with 7 mg of anhydrous sodium carbonate followed by addition of 23 mg of N-hydroxysuccinimide ester of L-4-benzyloxycarbonylamino-2-hydroxybutyric acid, and the admixture was allowed to stand at ambient temperature for 10 hours.

The reaction solution thus obtained was concentrated to a small volume and admixed with water, giving a solid precipitate. The solid was taken up into 3 ml of 2 N aqueous ammonia-tetrahydrofuran (5:3 by volume) and the solution was allowed to stand overnight at ambient temperature to effect the removal of the 3"-N-trifluoroacetyl group. The reaction mixture was concentrated to dryness to give a solid residue. This solid residue was dissolved in 4 ml of water-dioxane (1:1), and the solution was made weakly acidic by addition of a very small volume of acetic acid and subjected to catalytic hydrogenolysis with hydrogen at atmospheric pressure for one hour in the presence of palladium black catalyst to effect the removal of the benzyloxycarbonyl groups. The resultant reaction solution was filtered and concentrated, and the concentrate was passed through a column of CM-Sephadex C-25 ($NH_4^+$-form) (a product of Pharmacia Fine Chemicals Co., Sweden), which was then gradient-developed with 0→0.5 N aqueous ammonia. The fractions containing the desired product were combined together and concentrated to dryness to give 36 mg (Yield 89%) of the monocarbonate of the titled compound. The physiochemical properties and the antibacterial activities of this product were found to be perfectly identical to those of an authentic sample.

EXAMPLE 73

Synthesis of
1-N-[(L)-4-amino-2-hydroxybutyryl]-3'-deoxykanamycin A (a) Preparation of
3,6'-di-N-benzyloxycarbonyl-3'-deoxykanamycin A A suspension of 500 mg (1.07 millimol) of 3'-deoxykanamycin A (free base) in 12 ml of dimethylsulfoxide was admixed with 1 g (4.55 millimol) of zinc acetate dihydrate, and the resulting admixture was stirred until it formed a homogeneous solution. To this solution was added a solution of 610 mg (2.45 millimol) of N-benzyloxycarbonyloxysuccinimide in 5 ml of dimethylsulfoxide-tetrahydrofuran (1:1 by volume), and the reaction solution was then allowed to stand at ambient temperature overnight. Subsequently, the reaction solution was processed in substantially the same manner as in Example 72 (a) (iii), affording 765 mg (Yield 82%) of the above titled compound in the form of a colorless solid. $[\alpha]_D^{25} + 76°$ (c 1, water-dimethylformamide, 1:2).

Elemental analysis: Calcd. for $C_{34}H_{48}N_4O_{14} \cdot 2CH_3CO_2H \cdot H_2O$ C 52.16; H 6.68; N 6.40%. Found: C 51.99; H 6.75; N 6.20%.

(b) Preparation of
3,6'-di-N-benzyloxycarbonyl-3'-deoxy-3"-N-trifluoroacetylkanamycin A trifluoroacetate The product obtained in the above procedure (a) was processed as in Example 47 to give the titled compound.

(c) Preparation of
1-N-(L-4-amino-2-hydroxybutyryl)-3'-deoxykanamycin A

A solution of 50 mg of 3,6'-di-N-benzyloxycarbonyl3'-deoxy-3"-N-trifluoroacetylkanamycin A trifluoroacetate obtained in the above procedure (b) in 1.5 ml of water-tetrahydrofuran (1:2 by volume) was admixed with 6 mg of anhydrous sodium carbonate, followed by addition of 20 mg of N-hydroxysuccinimide ester of L-4-benzyloxycarbonylamino-2-hydroxybutyric acid. The admixture was allowed to stand at ambient temperature for 8 hours. The reaction solution was concentrated to a small volume and admixed with water, giving a solid precipitate.

The solid was admixed with 3 ml of 2 N-aqueous ammonia-tetrahydrofuran (1:1 by volume) and the admixture was allowed to stand overnight at ambient temperature to effect the removal of the 3"-N-trifluoroacetyl group. The reaction solution was concentrated to dryness to give a solid residue, and this residue was admixed with 4 ml of water-dioxane (1:1 by volume). The solution was made weakly acidic by addition of a very small volume of acetic acid and subjected to hydrogenolysis with hydrogen under atmospheric pressure for one hour over palladium black catalyst to effect the removal of benzyloxycarbonyl groups. Subsequently, the hydogenolysis reaction solution was processed in the same manner as in Example 72 (c), affording 30 mg (Yield 87%) of the titled compound as its monocarbonate monohydrate. $[\alpha]_D^{25} + 89°$ (c 1, water).

EXAMPLE 74

Synthesis of
1-N-(L-4-amino-2-hydroxybutyryl)-3',4'-dideoxykanamycin A

A solution of 70 mg of 3,6'-di-N-benzyloxycarbonyl-3',4'-dideoxy-3"-N-trifluoroacetylkanamycin A trifluoroacetate obtained in Example 52 in 2 ml of water-tetrahydrofuran (1:2) was admixed with 9 mg of anhydrous sodium carbonate, followed by addition of 28 mg of N-hydroxysuccinimide ester of L-4-benzyloxycarbonylamino-2-hydroxybutyric acid. The admixture was allowed to stand at ambient temperature for 10 hours. The reaction was concentrated to a small volume and admixed with water to give a solid precipitate.

The solid was admixed with 4 ml of a mixed solvent of 3 N aqueous ammonia-tetrahydrofuran (1:2), and the admixture was allowed to stand at ambient temperature overnight. The reaction solution was concentrated to dryness to give a solid residue. The residue was admixed with 6 ml of water-dioxane (1:3), and the solution was made weakly acidic by addition of a very small volume of acetic acid and subjected to hydrogenolysis with hydrogen at atmospheric pressure for 1.5 hours over palladium black catalyst added. Subsequently, the reaction solution was processed in the same manner as in Example 72 (c), affording 42 mg (Yield 91%) of the titled compound as its monocarbonate. $[\alpha]_D^{25} + 91°$ (c 1, water).

EXAMPLE 75

Synthesis of 1-N-(L-4-amino-2-hydroxybutyryl)tobramycin (a) Preparation of
3,2',6'-tri-N-benzyloxycarbonyltobramycin A suspension of 480 mg (1.03 millimol) of tobramycin (free base) in 12 ml of dimethylsulfoxide was admixed with 1 g (4.55 millimol) of zinc acetate dihydrate, and the admixture was stirred for one hour. To the reaction solution containing the tobramycin-zinc cation complex was dropwise added over about one hour a solution of 850 mg (3.4 millimol) of N-benzyloxycarbonyloxysuccinimide in 10 ml of tetrahydrofuran-dimethylsulfoxide (1:1 by volume), and the reaction mixture so formed was allowed to stand at ambient temperature overnight. The resulting reaction solution was treated with a large volume of ethyl ether in the same manner as in Example 72 (a) (ii), affording a thick syrupy product comprising the N-benzyloxycarbonylated tobramycinzinc complex. Subsequently, the syrupy complex product was processed in the same manner as in Example 72 (a) (iii) with excepting that the ratio of water-dioxane (2:1) was changed into 1:2 by volume. 810 mg (Yield 78%) of the titled compound in the form of a colorless solid was afforded. $[\alpha]_D^{25} + 65°$ (c 1, water-dimethylformamide, 1:2).

Elemental analysis: Calcd. for $C_{42}H_{55}N_5O_{15} \cdot 2CH_3CO_2H \cdot H_2O$: C 54.81; H 6.50; N 6.95%. Found: C 54.77; H 6.71; N 6.88%.

(b) Preparation of
3,2',6'-tri-N-benzyloxycarbonyl-3"-N-formyltobramycin monoformate The product obtained in the above procedure (a) was processed in the same manner as in Example 57 to give above the titled compound.

(c) Preparation of 1-N-(L-4-amino-2-hydroxybutyryl)tobramycin

A solution of 100 mg of 3,2',6'-tri-N-benzyloxycarbonyl-3"-N-formyltobramycin monoformate obtained in the above procedure (b) in 3 ml of water-tetrahydrofuran (1:3) was admixed with 12 mg of anhydrous sodium carbonate, followed by addition of 40 mg of N-hydroxysuccinimide ester of (L)-4-benzyloxycarbonylamino-2-hydroxybutyric acid. The admixture was allowed to stand at ambient temperature for 10 hours. The reaction solution so formed was concentrated to a small volume and admixed with water to deposit a solid precipitate.

The solid was suspended in 2 ml of 10% aqueous hydrogen peroxide, and the suspension was stirred vigorously at 60° C. for 3 hours and then filtered to afford a solid residue comprising the de-N-formyl derivative. The solid residue was taken up into 8 ml of water-dioxane (1:3), and the solution was made weakly acidic by addition of a very small volume of acetic acid and subjected to hydrogenolysis at atmospheric pressure for 1.5 hours over palladium black catalyst. Subsequently, the reaction solution was processed in the same manner as in Example 72 (c) and passed through the CM-Sephadex C-25 column, which was then gradientdeveloped with 0→1 N aqueous ammonia. The fractions containing the desired product were combined together and concentrated to dryness to give 67 mg (Yield 87%) of the above captioned compound as its dicarbonate dihydrate. $[\alpha]_D^{25} + 78°$ (c 1, water). This product was coincident with an authentic product.

EXAMPLE 76

Synthesis of
1-N-(L-4-amino-2-hydroxybutyryl)dibekacin (a) Preparation of
3,2',6'-tri-N-benzyloxycabonyldibekacin 600 mg (1.33 millimol) of dibekacin (free base) was admixed with 15 ml of dimethylsulfoxide under stirring. The solution was admixed with 1.4 g (6.4 millimol) of zinc acetate dihydrate under stirring. To the solution was dropwise added over about one hour a solution of 1.1 g (4.4 millimol) of N-benzyloxycarbonyloxysuccinimide in 12 ml of dimethylsulfoxide, and the admixture was allowed to stand at room temperature overnight. The resultant reaction solution was further admixed with a large volume of ethyl ether to give an oily deposit comprising mainly the desired product and a proportion of dimethylsulfoxide. The resultant oily deposit was separated from the upper liquid phase and further washed with ethyl to afford a thick syrupy product.

The syrupy product was washed repeatedly with water. With this water treatment, the initially existing excess of zinc acetate was removed and also the N-benzyloxycarbonylated zinc complex was destroyed, affording 1.1 g of a water-insoluble solid residue. This solid gave a single spot at Rf 0.13 in a silica gel thin layer chromatography developed with the lower phase of chloroform-methanol18% aqueous ammonia (1:1:1 by volume) as the development solvent and was comprising almost pure 3,2',6'-tri-N-benzyloxycarbonyldibekacin together with a trace of zinc incorporated therein. $[\alpha]_D^{25} + 71°$ (c 1, water-dimethylformamide, 1:2). If, however, the solid was washed with 3 M aqueous ammonia solution, pure product without contamination of zinc cation was obtained.

(b) Preparation of 3,2',6'-tri-N-benzyloxycarbonyl-3"-N-trifluoroacetylidebakacin trifluoroacetate The product of the above procedure (a) was processed as in Example 59 to afford the titled compound.

(c) Preparation of
1-N-(L-4-amino-2-hydroxybutyryl)dibekacin

A solution of 170 mg of 3,2',6'-tri-N-benzyloxycarbonyl-3''-N-trifluoroacetyldibekacin trifluoroacetate obtained in the above state (b) in 5 ml of water-tetrahydrofuran (1:3) was admixed with 18 mg of anhydrous sodium carbonate, followed by addition of 60 mg of N-hydroxysuccinimide ester of (S)-4-benzyloxycarbonylamino-2-hydroxybutyric acid, and the admixture was allowed to stand at ambient temperature for 9 hours. The reaction solution was concentrated to a small volume and admixed with water to deposit a solid precipitate.

The solid was admixed with 12 ml of 4 N aqueous ammonia-tetrahydrofuran (1:3) and the admixture was allowed to stand overnight at ambient temperature. The reaction solution was then concentrated to dryness to give a solid residue. The resultant solid was dissolved in 12 ml of water-dioxane (1:3), and the solution was made weakly acidic by addition of a very small amount of acetic acid and subjected to hydrogenolysis at atmospheric pressure for 1.5 hours over palladium black. Subsequently, the reaction solution was processed in the same manner as in Example 75 (c), affording 96 mg (Yield 89%) of the titled compound as its dicarbonate. $[\alpha]_D^{25}+86°$ (c 1, water). It was observed that the physicochemical properties and the antibacterial activities of this product was coincident with those of an authentic sample [Journal of Antibiotics Vol. 26, p 412 (1973)].

EXAMPLE 77

Synthesis of
1-N-(DL-3-amino-2-hydroxypropionyl)dibekacin, i.e.
1-N-DL-isoseryldibekacin A solution of 150 mg of 3,2',6'-tri-N-benzyloxycarbonyl-3''-N-trifluoroacetyldibekacin trifluoroacetate of Example 59 in 5 ml of water-tetrahydrofuran (1:3) was admixed with 16 mg of anhydrous sodium carbonate, followed by addition of 51 mg of N-hydroxysuccinimide ester of DL-3-benzyloxycarbonylamino-2-hydroxypropionic acid (i.e. DL-3-benzyloxycarbonylisoserine). The admixture was allowed to stand at ambient temperature for 10 hours. Subsequently, the reaction solution was processed in the same manner as in Example 76 (c), affording 82 mg (Yield 88%) of the titled compound as its dicarbonate. $[\alpha]_D^{25}+82°$ (c 0.32, water)

The physicochemical properties and the antibacterial activities of this product were found to be identical to those of an authentic sample.

EXAMPLE 78

Synthesis of
1-N-(L-4-amino-2-hydroxybutyryl)dibekacin (a) Preparation of
3,2',6'-tri-N-p-methoxybenzyloxycarbonyldibekacin 500 mg (1.11 m moles) of dibekacin (free base) was suspended in 15 ml of dimethylsulfoxide and the suspension was stirred to form a solution, to which was added 1.2 g (5.5 m moles) of zinc acetate dihydrate under stirring. To the resultant solution was dropwise added over about 30 minutes a solution of 1.17 g (3.86 m moles) of p-methoxycarbobenzoxy p-nitrophenyl ester dissolved in 10 ml of dimethylsulfoxide, and the mixture was allowed to stand overnight at room temperature. The resultant solution was then processed in the same manner as described in Example 76(a) to give 893 mg (Yield 85%) of the titled compound. $[\alpha]_D^{25}+69°$ (c 1, water-dimethylformamide, 1:2)

(b) Preparation of
3,2',6'-tri-N-p-methoxybenzyloxycarbonyl-3''-N-trifluoroacetyldibekacin trifluoroacetate A solution of 160 mg of 3,2',6'-tri-N-p-methoxybenzyloxycarbonyldibekacin in 2 ml of dimethylsulfoxide was admixed with 48 mg of ethyl trifluoroacetate, and the mixture was processed in the same manner as described in Example 33, affording 188 mg (Yield 96%) of the titled compound as a solid substance. $[\alpha]_D^{25}+58°$ (c 1, water-dimethylformamide, 1:2)

(c) Preparation of
1-N-(L-4-amino-2-hydroxybutyryl)dibekacin

A solution of 150 mg of 3,2'6'-tri-N-p-methoxybenzyloxycarbonyl-3''-N-trifluoroacetyldibekacin trifluoroacetate obtained in the above stage (b) dissolved in 5 ml of water-tetrahydrofuran (1:3) was admixed with 14 mg of anhydrous sodium carbonate, followed by addition of 54 mg N-hydroxysuccinimide ester of (S)-4-(p-methoxybenzyloxycarbonyl)amino-2-hydroxybutyric acid, and the mixture was allowed to stand at room temperature for 8 hours. The reaction solution was concentrated to a small volume and was admixed with water to deposit a solid precipitate.

To the solid was added a solution of 1 N-HCl in aqueous methanol (1:3, 6 ml), and the mixture was heated at 60° C. for 4 hours for removal of the p-methoxybenzyloxycarbonyl group. The solution was concentrated to a small volume, to which was added 5 N aqueous ammonia until the solution showed pH 10. The solution was allowed to stand at room temperature overnight and the solution was concentrated to give a residue. The residue was dissolved in water and the solution was charged on a column of CM-Sephadex C-25 (NH$_4^+$ form), which was washed with water thoroughly and then gradiently developed with 0→1 N aqueous ammonia. The fractions containing the desired product were combined together and concentrated to dryness to give 77 mg (Yield 87%) of the titled compound as its dicarbonate. $[\alpha]_D^{25}+85°$ (c 1, water).

What we claim is:

1. A process for the production of a selectively acylated N-protected derivative of an aminoglycosidic antibiotic, this aminoglycosidic antibiotic consisting essentially of a 6-0 (3''-amino- or 3''-alkylamino-3''-deoxyglycosyl)-2-deoxystreptamine having or not having a 4-0-(aminoglycosyl) group, and the selectively acylated N-protected derivative having all amino groups other than 1-amino and 3''-amino groups thereof selectively protected with an acyl group, which comprises the steps of:

(a) reacting an acylation reagent having an acyl group to be introduced as the amino-protecting group, with an aminoglycosidic antibiotic-zinc cation complex which has been formed by reaction of the aminoglycosidic antibiotic with a zinc salt in an inert organic solvent, to produce a complex of zinc cations with the selectively N-acylated derivative of the aminoglycosidic antibiotic having the initially non-complexed amino groups acylated, (b) and reacting the complex of zinc cations with the selectively N-acylated derivative of the aminoglycosidic antibiotic, with a reagent which removes zinc cations from said complex, to produce the desired selectively acylated N-protected derivative of the aminoglycosidic antibiotic.

2. A process as claimed in claim 1 in which the aminoglycosidic antibiotic is kanamycin A, 6'-N-alkylkanamycin A, 3'-deoxykanamycin A, 6'-N-methyl-3'-deoxykanamycin A, 4'-deoxykanamycin A, 6'-N-methyl-4'-deoxykanamycin A, 3',4'-dideoxykanamycin A, 6''-deoxykanamycin A, 4'',6''-dideoxykanamycin A; kanamycin B, 3'-deoxykanamycin B, 4'-deoxykanamycin B, 3',4'-dideoxykanamycin B, 3',4'-dideoxy-3'-eno-kanamycin B, 6'-N-methyl-3',4'-dideoxykanamycin B; kanamycin C, 3'-deoxykanamycin C, 3',4'-dideoxykanamycin C; gentamicin A, gentamicin B, gentamicin C; verdamicin; sisomicin or netilmicin.

3. A process as claimed in claim 1 in which formation of the aminoglycosidic antibiotic-zinc cation complex is performed by reacting zinc acetate or zinc chloride in a quantity of 2.3 to 6 mol. per mol. of the aminoglycosidic antibiotic in an inert organic solvent chosen from dimethylsulfoxide, aqueous dimethylsulfoxide, dimethylformamide, aqueous dimethylformamide, mixture of dimethylsulfoxide and dimethylformamide, tetrahydrofuran, aqueous tetrahydrofuran, methanol, aqueous methanol, ethanol and aqueous ethanol in the presence or absence of sodium acetate added.

4. A process as claimed in claim 1 in which the acyl group of the acylation reagent employed is an alkanoyl group, an aroyl group, an alkoxycarbonyl group, an aralkyloxycarbonyl group, an aryloxycarbonyl group, an alkylsulfonyl group, an aralkylsulfonyl group or an arylsulfonyl group known as the amino-protecting group.

5. A process as claimed in claim 1 in which the acylation reagent is employed in a molar quantity at least equal to the number of amino groups to be acylated in the aminoglycosidic antibiotic-zinc cation complex.

6. A process as claimed in claim 1 in which the complex of zinc cations with the selectively N-acylated aminoglycosidic antibiotic derivative is once separated from the acylation reaction mixture before it is reacted with a reagent of removing zinc cations from this complex.

7. A process as claimed in claim 1 in which the complex of zinc cations with the selectively N-acylated aminoglycosidic antibiotic derivative is separated from the acylation reaction mixture by extraction with an organic solvent, by evaporating the organic solvent medium from the acylation reaction mixture or by diluting the acylation reaction mixture with a diluent organic solvent, before it is reacted with a reagent of removing zinc cations.

8. A process as claimed in claim 1 in which the complex of zinc cations with the selectively N-acylated aminoglycosidic antibiotic derivative once separated is admixed with water or a polar organic solvent, either anhydrous or aqueous, which serves as the zinc cation-removing reagent.

9. A process as claimed in claim 8 in which the polar organic solvent is selected from the one in which the zinc salt is soluble but in which the N-acylated aminoglycosidic antibiotic derivative is insoluble, and the one in which the zinc salt is insoluble but in which the N-acylated aminoglycosidic antibiotic derivative is soluble.

10. A process as claimed in claim 1 in which the complex of zinc cations with the N-acylated aminoglycosidic antibiotic derivative once separated is again dissolved wholly in an organic solvent containing a proportion of water, and the resulting solution is subjected to a chromatographic procedure using a cation-exchange resin, an anion-exchange resin, chelate-exchange resin or a water-insoluble polymer containing functional groups capable of combining with a metal, which serves as the zinc cation-removing reagent.

11. A process as claimed in claim 1 in which the acylation reaction mixture is directly passed through a column of a cation-exchange resin, an anion-exchange resin, chelate-exchange resin or a water-insoluble polymer containing the metal-combining functions for adsorption of the complex of zinc cations with the N-acylated aminoglycosidic antibiotic derivative, and the column is then developed with an aqueous organic solvent of acid or base, and the eluate is collected in fractions, followed by recovery of the fractions containing the desired selectively N-acylated aminoglycosidic antibiotic derivative but containing no zinc cations.

12. A process as claimed in claim 1 in which when the desired N-acylated aminoglycosidic antibiotic derivative is insoluble or substantially insoluble in water, the acylation reaction mixture is immediately admixed with water, so that said derivative is precipitated separately from the zinc salt remaining dissolved in water.

13. A process as claimed in claim 1 in which the acylation reaction mixture is treated with hydrogen sulfide, an alkali metal sulfide or an alkaline earth metal sulfide which precipitates zinc cations as zinc sulfide, or with ammonium hydroxide which precipitates zinc cations as zinc hydroxide.

14. A process for the production of a selectively protected N-acylated derivative of an aminoglycosidic antibiotic consisting essentially of a 6-0-(3''-amino- or 3''-alkylamino-3''-deoxyglycosyl)-2-deoxystreptamine moiety having or not having a 4-0-(aminoglycosyl) group in which derivative 1-amino group of the deoxystreptamine moiety is unprotected but all the other amino groups in the amino-glycoside molecule are protected with same or different acyl groups; the process comprising a step of:

(a) reacting an alkanoic acid ester of the formula (VIII):

wherein $R^a$ is a hydrogen atom or a dihaloalkyl or trihaloalkyl group of 1–6 carbon atoms, and $R^b$ is an alkyloxy group of 1–6 carbon atoms, an aralkyloxy group, benzyloxy group or an aryloxy group, phenyloxy group, or an N-formylimidazole as the acylating agent in an inert organic solvent with a partially protected N-acylated derivative of the aminoglycosidic antibiotic in which 1-amino and 3''-amino or 3''-alkylamino groups are unprotected and all the other amino groups are protected with an acyl group as the amino-protecting group, to effect selective acylation of 3''-amino or 3''-alkylamino group of the partially protected N-acylated derivative with the acyl group $R^aCO-$ of said acylating agent and thereby give the desired 1-N-unprotected and other N-fully-protected derivative of the aminoglycosidic antibiotic.

15. A process as claimed in claim 14 in which the alkanoic acid ester of the formula (VIII) is reacted with the partially protected N-acylated derivative of kanamycin A, 6'-N-alkylkanamycin A, 3'-deoxykanamycin A, 6'-N-methyl-3'-deoxykanamycin A, 4'-deoxykanamycin A, 6'-N-methyl-4'-deoxykanamycin A, 3',4'-dideoxykanamycin A, 6''-deoxykanamycin A, 4'',6''-dideoxykanamycin A; kanamycin B, 3'-deoxykanamycin B, 4'-deoxykanamycin B, 3',4'-dideoxykanamycin B, 3',4'-dideoxy-3'-eno-kanamycin B, 6'-N-methyl-3',4'-dideoxykanamycin B; kanamycin C, 3'-deoxykanamycin C, 3',4'-dideoxykanamycin C; gentamicin A, gentamicin B, gentamicin C; verdamicin; sisomicin or netilmicin.

16. A process as claimed in claim 14 in which the alkanoic acid ester of the formula (VIII) is selected as the acylating agent from methyl formate, ethyl formate, butyl formate, benzyl formate, phenyl formate, methyl dichloroacetate, ethyl dichloroacetate, methyl trichloroacetate, phenyl trichloroacetate, methyl trifluoroacetate, ethyl trifluoroacetate or phenyl trifluoroacetate.

17. A process as claimed in claim 14 in which N-formylimidazole is employed as the acylating agent.

18. A process as claimed in claim 14 in which the acylating agent is reacted at a temperature of $-30°$ C. to $+120°$ C. for a time of 30 minutes to 24 hours or even to 48 hours in an inert organic solvent selected from dimethylsulfoxide, dimethylformamide, hexamethylphosphoric triamide, tetrahydrofurane, dioxane, acetonitrile, nitromethane, sulfolane, dimethylacetamide, chloroform, dichloromethane, methanol, ethanol, n-butanol, t-butanol, benzene, toluene or ethyl ether, which is either anhydrous or aqueous.

19. An improved process for producting a 1-N-($\alpha$-hydroxy-$\omega$-aminoalkanoyl) derivative of an aminoglycosidic antibiotic consisting essentially of a 6-0-(3''-amino- or 3''-alkylamino-3''-deoxyglycosyl)-2-deoxystreptamine moiety having or not having a 4-0-(aminoglycosyl) group, the process comprising the consecutive steps of:

(a) reacting zinc cations with the aminoglycosidic antibiotic in an inert organic solvent to produce the complex of zinc cations with the aminoglycosidic antibiotic, (b) reacting an acylating reagent having an acyl group to be introduced as the amino-protecting group, with the aminoglycosidic antibiotic-zinc cation complex formed in the above step (a) in situ in the inert organic solvent, to produce a complex of zinc cations with the selectively N-acylated derivative of the aminoglycosidic antibiotic having the initially non-complexed amino groups acylated, (c) reacting the selectively N-acylated aminoglycosidic antibiotic derivative-zinc cation complex obtained in the above step (b), with a reagent which removes zinc cations from the N-acylated zinc complex, to give a partially and selectively protected N-acylated aminoglycosidic antibiotic derivative which is free from zinc cations, and in which 1-amino and 3''-amino or 3''-alkylamino groups are unprotected but all the other amino groups in the aminoglycoside molecule are protected by the acyl group, (d) reacting the partially and selectively protected N-acylated derivative obtained in the above step (c) with an alkanoic acid ester of the formula (VIII):

wherein $R^a$ is a hydrogen atom or a dihaloalkyl or trihaloalkyl group of 1–6 carbon atoms and $R^b$ is an alkyloxy group of 1–6 carbon atoms, an aralkyloxy group of 1–6 carbon atoms or an aryloxy group, or N-formylimidazole as the acylating agent in an inert organic solvent to selectively acylate the 3''-amino or 3''-alkylamino group with the acyl group $R^aCO$— of said acylating agent and thereby to give the 1-N-unprotected and other N-fully-acylated-protected derivative of the aminoglycosidic antibiotic in which all the amino groups other than 1-amino group are protected with acyl group, (e) reacting the 1-N-unprotected and other N-fully-protected derivative obtained in the preceding step (d) with an $\alpha$-hydroxy-$\omega$-aminoalkanoic acid of the formula (IX):

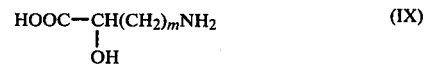

wherein m is 1 or 2 or an equivalent reactive derivative thereof of which the amino group is either unprotected or protected, to acylate 1-amino group of said 1-N-unprotected derivative, (f) and then removing the residual amino-protecting groups from the 1-N-acylation product obtained in the above step.

20. A process as claimed in claim 1 wherein the inert organic solvent contains an acid or base.

* * * * *